(12) United States Patent
Bhatt et al.

(10) Patent No.: US 10,959,985 B1
(45) Date of Patent: *Mar. 30, 2021

(54) PHARMACEUTICAL COMPOSITIONS INCLUDING CARVEDILOL AND METHODS OF USING THE SAME

(71) Applicant: ECI Pharmaceuticals, LLC, Fort Lauderdale, FL (US)

(72) Inventors: Nirali R. Bhatt, Pompano Beach, FL (US); Solomon Goll, Davie, FL (US)

(73) Assignee: ECI Pharmaceuticals, LLC, Fort Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/987,443

(22) Filed: Aug. 7, 2020

Related U.S. Application Data

(63) Continuation of application No. 16/743,420, filed on Jan. 15, 2020, now Pat. No. 10,772,869.

(60) Provisional application No. 62/878,048, filed on Jul. 24, 2019.

(51) Int. Cl.
| | | |
|---|---|---|
| *A61K 31/403* | (2006.01) | |
| *A61K 9/00* | (2006.01) | |
| *A61K 47/40* | (2006.01) | |

(52) U.S. Cl.
CPC .......... *A61K 31/403* (2013.01); *A61K 9/0053* (2013.01); *A61K 47/40* (2013.01)

(58) Field of Classification Search
None
See application file for complete search history.

(56) References Cited

U.S. PATENT DOCUMENTS

| | | |
|---|---|---|
| 6,515,010 B1 | 2/2003 | Franchini et al. |
| 6,852,337 B2 | 2/2005 | Gabel et al. |
| 7,268,156 B2 | 9/2007 | Brook et al. |
| RE40,000 E | 1/2008 | Lukas-Laskey et al. |
| 7,417,038 B1 | 8/2008 | Anker et al. |
| 7,485,663 B2 | 2/2009 | Hildesheim et al. |
| RE40,707 E | 5/2009 | Lukas-Laskey et al. |
| 7,626,041 B2 | 12/2009 | Brook et al. |
| 7,649,010 B2 | 1/2010 | Chen et al. |
| 7,750,036 B2 | 7/2010 | Brook et al. |
| 7,759,384 B2 | 7/2010 | Brook et al. |
| 7,763,645 B2 | 7/2010 | Sanganabhatla et al. |
| 7,893,100 B2 | 2/2011 | Brook et al. |
| 7,902,378 B2 | 3/2011 | Brook et al. |
| 8,022,094 B2 | 9/2011 | Ini et al. |
| 8,114,900 B2 | 2/2012 | Ini et al. |
| 8,124,644 B2 | 2/2012 | Levi |
| 8,278,461 B2 | 10/2012 | Thaper et al. |
| 8,344,159 B2 | 1/2013 | Gorantla et al. |
| 8,367,112 B2 | 2/2013 | Liversidge et al. |
| 8,449,914 B2 | 5/2013 | Andersen et al. |
| 8,889,728 B2 | 11/2014 | Guha et al. |
| 8,987,262 B2 | 3/2015 | Leaute-Labreze et al. |
| 10,772,869 B1 | 9/2020 | Bhatt et al. |
| 2018/0280323 A1 | 10/2018 | Bond et al. |

FOREIGN PATENT DOCUMENTS

WO  WO 03/028718 A1  4/2003

OTHER PUBLICATIONS

Loftsson et al., AAPS PharmSciTech (2008), 9(2), pp. 425-430.*
Feng et al., Yaoxue Jinzhan (2013), 37(9), pp. 460-463.*
Anonymous, Carvedilol Monograph for Professionals—Drugs.com/monograph/carvedilol, retrieved from internet Mar. 2, 2020.*
U.S. Appl. No. 60/326,368, filed Oct. 1, 2001.
Labeling package insert for COREG (carvedilol) tablets for oral use, Sep. 14, 2017, accessed from https://www.accessdata.fda.gov/scripts/cder/daf/index.cfm?event=overview.process&ApplNo=020297, 35 pages.
Labeling package insert for COREG CR (carvedilol phosphate) extended-release capsules for oral use, Sep. 14, 2017, accessed from https://www.accessdata.fda.gov/scripts/cder/daf/index.cfm?event=overview.process&ApplNo=022012, 39 pages.
Drug Label Information for COREG CR—carvedilol phosphate capsule, extended release, Nov. 1, 2019, accessed from https://dailymed.nlm.nih.gov/dailymed/lookup.cfm?setid=06400a4c-42b4-440a-92b4-1f47f98ac7ba, 57 pages.
Loftsson et al., Carvedilol: Solubilization and Cyclodextrin Complexation: A Technical Note, AAPS PharmSciTech, vol. 9, No. 2, 2008, pp. 425-430.
Feng et al., Solubilization of 2-hydroxypropyl-β-cyclodextrin for carvedilol, American Chemical Society, SciFinder abstract, database CAPLUS, Acc.. No. 2014:201152, Yaoxue Jinzhan Blanjibu, vol. 37, No. 9, 2013, 1 page.
Anonymous, Carvedilol Monograph for Professionals—Drugs.com/monograph/carvedilol, retrieved from internet Mar. 2, 2020, 21 pages.
Feng, et al., Study on the Solubilization of 2-hydroxypropyl-β-cyclodextrin for Carvedilol, Progress in Pharmaceutical Sciences, 2013, vol. 37, No. 9, 2013, pp. 460-463.

* cited by examiner

*Primary Examiner* — Brian J Davis
(74) *Attorney, Agent, or Firm* — K&L Gates LLP

(57) ABSTRACT

The present disclosure provides oral liquid compositions including carvedilol with enhanced solubility and stability. Also provided herein are methods of using oral liquid compositions for the treatment of hypertension, treatment of heart failure, and reduction of cardiovascular mortality in clinically stable patients with left ventricular failure or left ventricular dysfunction following myocardial infarction.

30 Claims, 3 Drawing Sheets

PHARMACEUTICAL COMPOSITIONS INCLUDING CARVEDILOL AND METHODS OF USING THE SAME

CROSS-REFERENCE TO RELATED APPLICATIONS

The present application claims priority under 35 U.S.C. § 120 to U.S. patent application Ser. No. 16/743,420, filed Jan. 15, 2020, now issued as U.S. Pat. No. 10,772,869, which in turn claims priority under 35 U.S.C. § 119(e) to U.S. Provisional Patent Application Ser. No. 62/878,048, filed Jul. 24, 2019. The entire disclosure of each such application is hereby incorporated by reference herein.

FIELD OF THE INVENTION

The present disclosure relates to pharmaceutical compositions including carvedilol and methods of use thereof.

BACKGROUND

Carvedilol has the systemic name of (±) 1-(9H-carbazol-4-yloxy)-3-[[2(2-methoxyphenoxy)ethyl]amino]-2-propanol, (CAS Registry No. 72956-09-3). As shown in FIG. 1, the structure of carvedilol has a chiral center. Carvedilol is a racemic mixture of R(+) and S(−) enantiomers, where α-adrenergic blocking activity is present in both R(+) and S(−) enantiomers and non-selective β-adrenoreceptor blocking activity is present in the S(−) enantiomer.

Carvedilol is a non-selective β-adrenergic blocking agent used clinically for treating cardiovascular diseases (heart failure and hypertension). Its vasodilator properties are attributed to a1-blocking activity, as is its capacity to inhibit oxidative stress in coronary smooth muscle. Although carvedilol has been tested only in adults, several studies report that it is effective in children with heart failure.

The only currently available oral formulation of carvedilol is in dosage tablet form. COREG® tablets were approved by the FDA on Sep. 14, 1995 for treatment of congestive heart failure and hypertension in adults. Extemporaneous suspensions including carvedilol have been prepared by reconstituting crushed COREG® tablets in deionized water and sorbitol 70% or with ORA-SWEET® oral syrup vehicle and ORA-PLUS® oral suspending vehicle, resulting in carvedilol concentrations of 0.625 and 1.25 mg/ml, respectively. It has been reported that these suspensions have limited stability.

Carvedilol is practically insoluble in water, and hence is routinely compounded in liquid form with limited shelf life for patients who may have trouble swallowing tablets or require specific dose titration. Currently, there is no FDA approved oral carvedilol liquid formulation.

However, some patients, specifically pediatric and geriatric patient populations, may dislike or have difficulty swallowing solid oral dosage forms, which can lead to associated disadvantages, such as patient non-compliance. In such situations, oral liquid dosage forms, including solutions, suspensions and emulsions, can be easier to administer and more suitable for use.

Poor bioavailability of pharmaceuticals presents a major challenge in designing oral dosage forms. The oral bioavailability depends on several factors, including aqueous solubility, drug permeability, dissolution rate, first-pass metabolism, presystemic metabolism, and susceptibility to efflux mechanisms. The most frequent causes of low oral bioavailability are attributed to poor solubility and low permeability.

For orally administered drugs, solubility is the most important rate limiting parameter to achieve a desired concentration in systemic circulation for pharmacological response. Accordingly, liquid compositions containing active pharmaceutical ingredients that are completely solubilized in a liquid composition are more advantageous over suspensions. The extent of solubility of a substance in a specific solvent is measured as the saturation concentration, at which the addition of more solute does not increase its concentration in solution. The extent of solubility ranges widely, from infinitely soluble (fully miscible) (for example, ethanol in water) to poorly soluble (for example, silver chloride in water). Solubility is based on the highest-dose strength of an immediate release product. A drug is considered highly soluble when the highest dose strength is soluble in 250 mL or less of aqueous media over the pH range of 1 to 7.5.

Accordingly, there remains a need for a highly bioavailable, highly soluble, stable carvedilol oral solution that can address these problems, while safely and effectively providing proper and consistent administration of carvedilol with accuracy and precision to patients who have difficulty swallowing solid dosage forms.

SUMMARY

Provided herein are stable oral liquid compositions including carvedilol. In one aspect, the present disclosure provides an oral liquid composition including about 0.05 mg/mL to about 15.0 mg/mL carvedilol or a pharmaceutically acceptable salt or solvate thereof, about 1.0 mg/mL to about 50 mg/mL cyclodextrin, about 0.0020 mg/mL to about 38 mg/mL acid, and water is provided herein.

In some embodiments, the pH of the oral liquid composition is about 1.0 to about 5.0. In certain embodiments, the cyclodextrin can be or include hydroxypropyl beta-cyclodextrin. In certain embodiments, the oral liquid composition retains at least about 90% of an initial carvedilol amount when stored at a temperature ranging from about 22° C. to about 28° C. and a relative humidity ("RH") ranging from about 34% to about 47% for at least 3 months.

In another aspect, the present disclosure provides an oral liquid composition including about 0.05 mg/mL to about 15.0 mg/mL carvedilol or a pharmaceutically acceptable salt or solvate thereof, about 1.0 mg/mL to about 50 mg/mL hydroxypropyl beta-cyclodextrin, about 0.5 mg/mL to about 20 mg/mL glacial acetic acid, and water.

In another aspect, the present disclosure provides methods of treating hypertension comprising administering to a patient in need thereof an oral liquid composition about 0.05 mg/mL to about 15.0 mg/mL carvedilol or a pharmaceutically acceptable salt or solvate thereof, about 1.0 mg/mL to about 50 mg/mL hydroxypropyl beta-cyclodextrin, about 0.0020 mg/mL to about 38 mg/mL glacial acetic acid, and water.

In another aspect, methods of treating heart failure comprising administering to a patient in need thereof an oral liquid composition including about 0.05 mg/mL to about 15.0 mg/mL carvedilol or a pharmaceutically acceptable salt or solvate thereof, about 1.0 mg/mL to about 50 mg/mL hydroxypropyl beta-cyclodextrin, about 0.0020 mg/mL to about 38 mg/mL glacial acetic acid, and water are provided herein.

In yet another aspect, methods of reducing cardiovascular mortality in clinically stable patients with left ventricular failure or left ventricular dysfunction following myocardial infarction comprising administering to a patient in need thereof an oral liquid composition including about 0.05 mg/mL to about 15.0 mg/mL carvedilol or a pharmaceutically acceptable salt or solvate thereof, about 1.0 mg/mL to about 50 mg/mL hydroxypropyl beta-cyclodextrin, about 0.0020 mg/mL to about 38 mg/mL glacial acetic acid, and water are provided herein.

BRIEF DESCRIPTION OF THE DRAWINGS

Various features and characteristics of non-limiting and non-exhaustive embodiments disclosed and described in this specification may be better understood by reference to the accompanying figures, in which:

FIGS. 2A and 2B are views of a non-limiting embodiment of a 4 ounce polyethylene terephthalate resin container used to contain an oral liquid composition, as described herein, wherein FIG. 2A is an isometric view of the container and FIG. 2B is an elevational view of the container.

FIGS. 3A and 3B are views of a container closure that can be used in conjunction with the container shown in FIGS. 2A and 2B, wherein FIG. 3A is an exterior elevational view of a ribbed, threaded closure cap and FIG. 3B is a section view of the cap shown in FIG. 3A.

DETAILED DESCRIPTION

Figure 1:
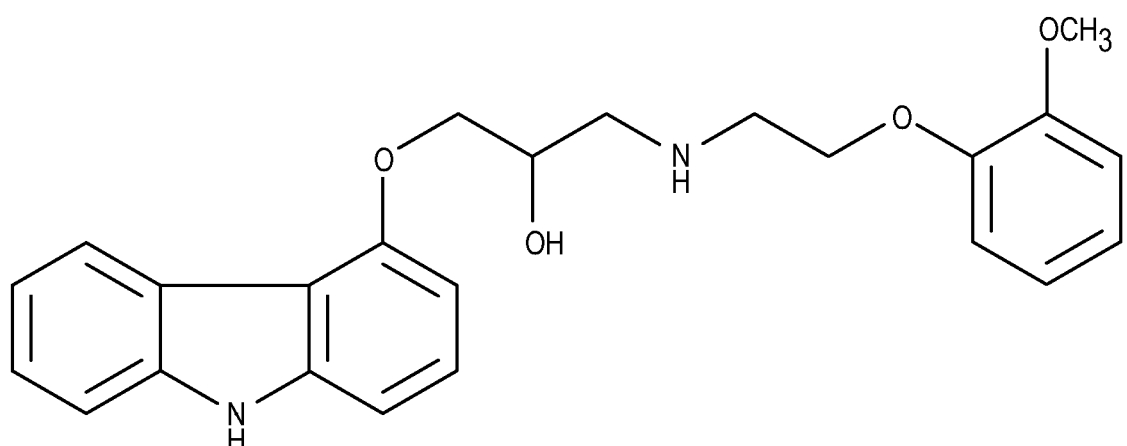
FIG. 1 shows the chemical structure of carvedilol, also known as (±) 1-(9H-carbazol-4-yloxy)-3-[[2(2-methoxyphenoxy)ethyl]amino]-2-propanol, (CAS Registry No. 72956-09-3).
Figure 2A:
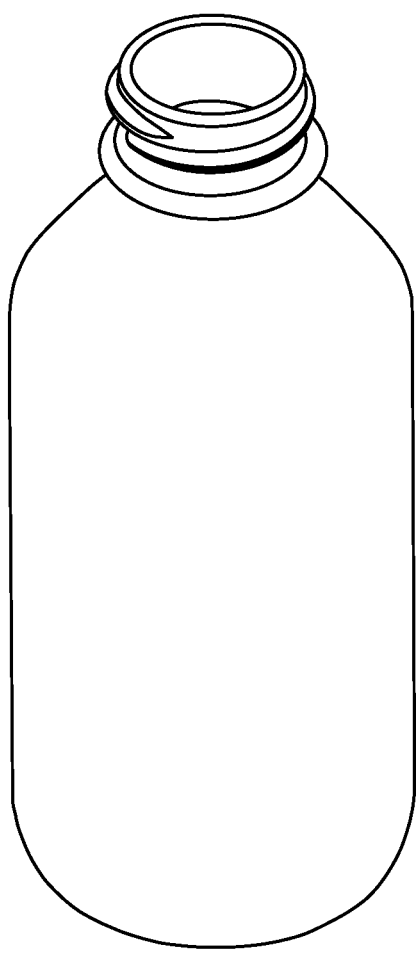
Figure 2B:
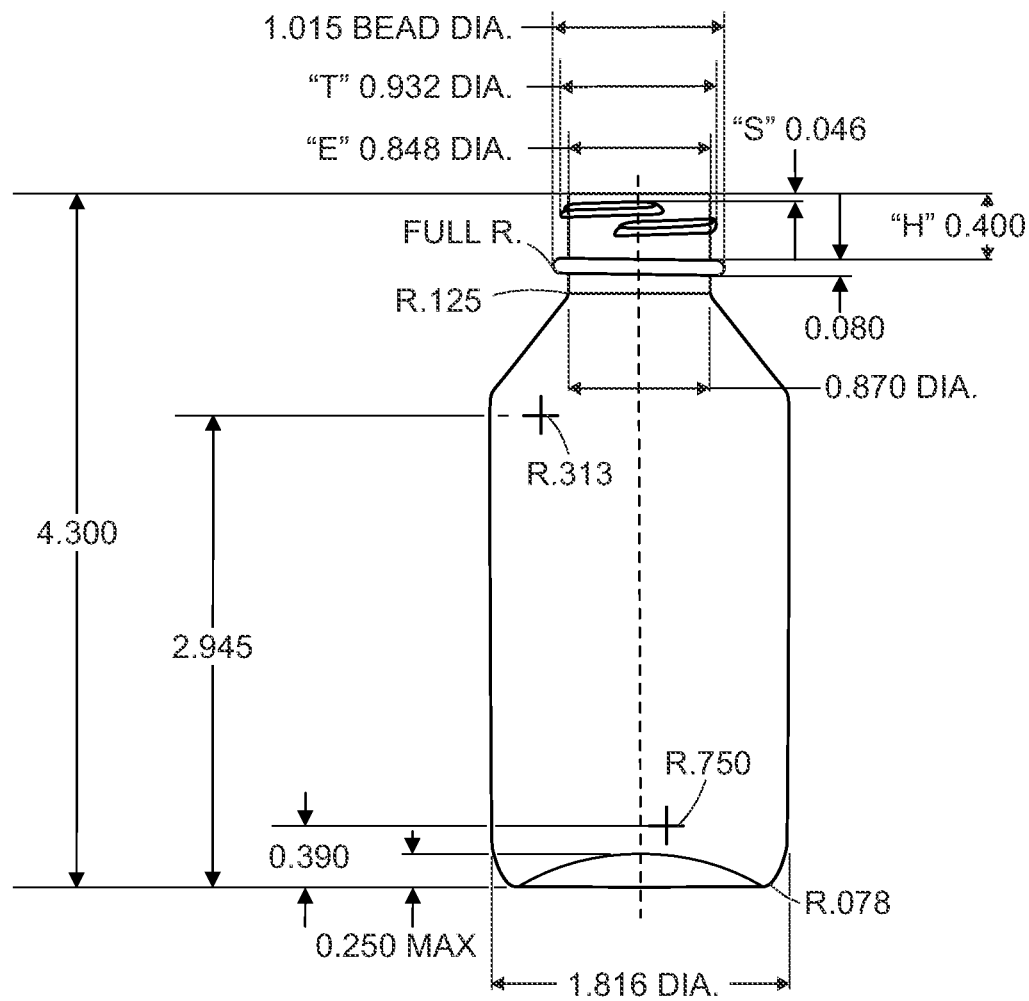

Provided herein are stable oral liquid compositions including carvedilol. Such compositions can be useful in the treatment of hypertension, congestive heart failure and angina. The compositions can provide advantages over conventional oral solid dosage administration of carvedilol including, for example, ease of administration, improved absorption, increased patient compliance, and accurate/precise delivery of carvedilol to the patient. Further, in various non-limiting embodiments carvedilol is fully solubilized in the oral liquid compositions, providing oral liquid compositions that have improved bioavailability over liquid compositions that are suspensions, in which carvedilol is not fully solubilized.

As used herein, the terms "suspension" and "suspensions" refer to liquid formulations in which solute particles of a substance in the formulations are suspended within a solvent and thus remain undissolved in the formulations. The degree to which a substance will dissolve in a solvent to result in a solution is known as solubility. Solubility is the property of a solute that is a solid, liquid, or gas to dissolve in a solid, liquid, or gaseous solvent. The solubility of a substance fundamentally depends on the physical and chemical properties of the solute and the solvent, as well as on temperature, pressure, and presence of other chemicals (including changes to the pH) of the solution. As used herein, the phrase "fully solubilized" refers to the complete solubilization of a solute at a particular concentration in a solvent.

As used herein, "carvedilol" refers to any of carvedilol base, its salt, solvate, derivative isomer, and polymorph thereof. Suitable compounds include the free base, organic and inorganic salts, isomers, isomer salts, solvates, polymorphs, amorphous forms, and complexes of carvedilol. Carvedilol can be purchased from commercial sources or can be prepared according to methods described herein.

Certain segments of the population have difficulty ingesting and swallowing solid oral dosage forms leading to non-compliance with the recommended therapy with solid dosage forms and this can result in less-than-effective therapy. Additionally, there is an increased risk of choking when children or the elderly are administered solid dosage forms.

A compounding pharmacist can prepare current liquid preparations of carvedilol by grinding carvedilol solid dosage forms into a powder and mixing the powder in a liquid. However, forming carvedilol liquid compositions using such techniques can have significant drawbacks, including forming suspensions rather than solutions, large variability in the actual dosage amount of carvedilol, incomplete or inconsistent suspension of the carvedilol solid dosage form in the liquid, rapid instability, inconsistent formulation methods per compounding pharmacist, shelf life for patients requiring specific dose titration, and several other potential issues.

It has now been discovered that an oral liquid composition including carvedilol that has a pH of about 2.0 to about 3.5 and includes hydroxypropyl β-cyclodextrin surprisingly and unexpectedly exhibits markedly improved solubility and stability of carvedilol in the composition. For example, the present inventors found that oral liquid compositions including carvedilol in concentrations ranging from about 0.8 mg/mL to about 12 mg/mL, about 0.9 mg/mL to about 11 mg/mL, or about 1.25 mg/mL to about 10 mg/mL were surprisingly and unexpectedly fully solubilized at pH 1.5 to pH 4.0, at pH 1.75 to 3.75, at pH 2.5 to pH 3.5, at pH 2.5 to pH 3.0, at pH 2.75 to pH 3.25, or pH 2.8 to pH 3.5. Further, it was discovered that oral liquid compositions including carvedilol and also including hydroxypropyl β-cyclodextrin in a concentration of about 40 mg/5 mL to about 60 mg/5 mL, or in weight percentages ranging from about 0.5% to about 3.0%, about 0.75% to about 2.75%, about 0.8% to about 2.2%, about 1% to about 2.0%, about 1.5% to about 2.5%, or about 1% to about 2.25%, based on total weight of the composition, exhibit surprising and unexpected stability for up to about 3 months, up to about 4 months, up to about 5 months, up to about 6 months, up to about 9 months, up to about 12 months, up to about 18 months, or in some cases even longer.

Embodiments of oral liquid compositions provided herein allow for safe and effective administration of carvedilol for the treatment of conditions including, for example, hypertension, congestive heart failure, and angina.

In certain embodiments, the carvedilol used in compositions disclosed herein is or includes carvedilol-free base. In various embodiments, the carvedilol used in compositions disclosed herein is or includes a carvedilol salt. In certain embodiments, the carvedilol used in compositions disclosed herein is or includes a solvate of carvedilol.

Oral Liquid Compositions Containing Carvedilol:

In one aspect according to the present disclosure, certain oral liquid compositions comprise carvedilol and a combination of a cyclodextrin and an acid. The cyclodextrin is a controlled release and stability agent, and the acid is used to adjust the pH of the composition. The cyclodextrin and acid are present in the oral liquid compositions in concentrations to provide an unexpectedly highly solubilized and stable composition. In certain non-limiting embodiments, the oral liquid compositions are substantially free of solids, whereby all components are fully solubilized in the compositions. The phrase "substantially free of solids", as used herein, refers to the characteristic wherein a solution is essentially devoid of solid, undissolved particulates.

In certain non-limiting embodiments of oral liquid compositions according to the present disclosure, carvedilol is present in a concentration of about 0.05 mg/mL to about 15.0 mg/mL, or at any concentration or within any concentration range subsumed therein. In certain non-limiting embodiments, carvedilol is present in oral liquid compositions according to the present disclosure in a concentration of 0.05 mg/mL to about 12.0 mg/mL, 0.05 mg/mL to about 5.0 mg/mL, 0.05 mg/mL to about 3.5 mg/mL, 0.05 mg/mL to about 2.7 mg/mL, 0.05 mg/mL to about 2.0 mg/mL, 0.05 mg/mL to about 1.50 mg/mL, about 0.07 mg/mL to about 12 mg/mL, about 0.07 mg/mL to about 5.0 mg/mL, about 0.07 mg/mL to about 3.0 mg/mL, about 0.07 mg/mL to about 2.0 mg/mL, about 0.10 mg/mL to about 13.0 mg/mL, about 0.12 mg/mL to about 4.0 mg/mL, about 0.15 mg/mL to about 7.0 mg/mL, about 0.20 mg/mL to about 10.0 mg/mL, about 0.5 mg/mL to about 8.0 mg/mL, about 0.75 mg/mL to about 12 mg/mL, about 0.75 mg/mL to about 6.0 mg/mL, about 0.75 mg/mL to about 3.5 mg/mL, about 0.75 mg/mL to about 2.7 mg/mL, about 0.75 mg/mL to about 2.0 mg/mL, about 0.75 mg/mL to about 1.7 mg/mL, about 0.80 mg/mL to about 3.0 mg/mL, about 1.0 mg/mL to about 5.0 mg/mL, about 1.7 mg/mL to about 3.5 mg/mL, about 2.0 mg/mL to about 11 mg/mL, about 5.0 mg/mL to about 15 mg/mL, about 7.5 mg/mL to about 12.5 mg/mL, or about 9.0 mg/mL to about 11 mg/mL, all based on the total volume of the oral liquid composition. In certain non-limiting embodiments, carvedilol is present in a concentration of about 1.25 mg/mL based on the total volume of the oral liquid composition.

In certain non-limiting embodiments of oral liquid compositions according to the present disclosure, carvedilol is present in a concentration of from about 0.005% w/w to about 2.0% w/w based on the total weight of the solids used to prepare the oral liquid composition, or at any concentration or within any concentration range subsumed therein. In certain non-limiting embodiments, carvedilol is present in a concentration of about 0.0075% w/w to about 5.0% w/w based on the total weight of the solids used to prepare the oral liquid composition. In various non-limiting embodiments, carvedilol is present in the oral liquid compositions in a w/w concentration, based on the total weight of solids used to prepare the oral liquid composition, ranging from about 0.01% to about 2.5%, about 0.025% to about 3.0%, about 0.05% to about 1.5%, about 0.07% to about 1.2%, about 0.08% to about 1.4%, about 0.09% to about 2.5%, or about 0.10% to about 2.3%. In certain non-limiting embodiments, carvedilol is present in the oral liquid compositions in a w/w concentration, based on the total weight of solids used to prepare the composition, of about 0.125%.

The present inventors discovered that cyclodextrin complexing agents may be included in oral liquid compositions according to the present disclosure to increase the bioavailability and stability of the relatively poorly water soluble or unstable carvedilol. Surprisingly, the inventors found that cyclodextrins have the ability to form inclusion complexes with carvedilol by entrapping the carvedilol molecules (the "guest") inside a cyclodextrin cavity, which acts as a "host". The term "complex" as used herein refers to a compound of carvedilol associated with a cyclodextrin through a form of intermolecular non-covalent bond.

In certain non-limiting embodiments, the oral liquid composition includes hydroxypropyl beta-cyclodextrin. In certain non-limiting embodiments, the oral liquid composition includes at least one of an alpha-cyclodextrin, a beta-cyclodextrin, a gamma-cyclodextrin, or the like. For example, an oral liquid composition according to the present disclosure may include one or more of hydroxypropyl beta-cyclodextrin, sulfobutylether-beta-cyclodextrin, methyl-beta-cyclodextrin (MβCD), polymeric derivatives of β cyclodextrins such as polyethylene glycol (βCD-PEG), and dextran-βCD (βCD-dextran).

In certain non-limiting embodiments, cyclodextrin is present in oral liquid compositions according to the present disclosure in concentrations that provide surprising and unexpected stability. Such cyclodextrin concentrations include, for example, about 1.0 mg/mL to about 50 mg/mL of the oral liquid composition, or in any concentration or within any concentration range subsumed therein. In certain non-limiting embodiments, cyclodextrin is present in oral liquid compositions according to the present disclosure in a concentration ranging from about 0.5 mg/mL to about 100 mg/mL, about 0.5 mg/mL to about 50 mg/mL, about 0.5 mg/mL to about 30 mg/mL, about 0.5 mg/mL to about 25 mg/mL, about 0.5 mg/mL to about 14 mg/mL, about 0.75 mg/mL to about 50 mg/mL, about 1 mg/mL to about 30 mg/mL, about 3 mg/mL to about 25 mg/mL, about 3 mg/mL to about 15 mg/mL, about 5 mg/mL to about 23 mg/mL, about 5 mg/mL to about 20 mg/mL, about 5 mg/mL to about 17 mg/mL, about 5 mg/mL to about 12 mg/mL, about 7 mg/mL to about 30 mg/mL, about 7 mg/mL to about 25 mg/mL, about 7 mg/mL to about 20 mg/mL, about 7 mg/mL to about 18 mg/mL, about 7 mg/mL to about 15 mg/mL, about 7 mg/mL to about 12 mg/mL, about 8 mg/mL to about 40 mg/mL, about 8 mg/mL to about 30 mg/mL, about 8 mg/mL to about 25 mg/mL, about 8 mg/mL to about 21 mg/mL, about 8 mg/mL to about 18 mg/mL, about 8 mg/mL to about 15 mg/mL, about 8 mg/mL to about 12 mg/mL, about 18 mg/mL to about 22 mg/mL, or about 19 mg/mL to about 21 mg/mL, all based on the total volume of the oral liquid composition. In certain non-limiting embodiments, hydroxypropyl beta-cyclodextrin is present in the oral liquid composition in a concentration of about 10.0 mg/mL based on the total volume of the oral liquid composition.

In certain non-limiting embodiments of oral liquid compositions according to the present disclosure, cyclodextrin is present in a concentration ranging from about 0.01% w/w to about 12% w/w based on the total weight of solids used to prepare the oral liquid composition, or in any concentration or within any concentration range subsumed therein. In other non-limiting embodiments, cyclodextrin is present in a concentration ranging from about 0.075% w/w to about 10% w/w based on the total weight of solids used to prepare the oral liquid composition. In various non-limiting embodiments, cyclodextrin is present in a concentration ranging from about 0.025% to about 5%, about 0.05% to about 10%, about 0.10% to about 9.0%, about 0.25% to about 8.0%, about 0.40% to about 7.0%, about 0.5% to about 6.0%, about 0.6% to about 5.0%, about 0.8% to about 3.0%, or about 0.30% to about 6.0% w/w, all based on the total weight of solids used to prepare the oral liquid composition. In certain non-limiting embodiments, cyclodextrin is present in the oral liquid composition in a concentration of about 1.00% w/w based on the total weight of solids used to prepare the oral liquid composition.

In certain non-limiting embodiments of oral liquid compositions according to the present disclosure, acid is incorporated into the oral liquid composition. In certain non-limiting embodiments the acid can include one or more of glacial acetic acid, hydrochloric acid, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, anhydrous citric acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (− L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (− L), salicylic acid, sebacic acid, stearic acid, succinic acid, sulfuric acid, tartaric acid (+ L), thiocyanic acid, toluenesulfonic acid (p), undecylenic acid, and the like. In one non-limiting embodiment, the oral liquid composition includes glacial acetic acid and/or hydrochloric acid.

In certain non-limiting embodiments of oral liquid compositions according to the present disclosure, acid is incorporated in the oral liquid composition in a concentration ranging from about 0.005% w/w to about 3.0% w/w based on the total weight of solids used to prepare the oral liquid composition, or in any concentration or within any concentration range subsumed therein. In certain non-limiting embodiments, acid is present in the oral liquid composition in a concentration of about 0.0075% w/w to about 2.0% w/w based on the total weight of the solids used to prepare the oral liquid composition. In various non-limiting embodiments of oral liquid compositions according to the present disclosure, acid is present in a w/w concentration, based on the total weight of solids used to prepare the oral liquid composition, ranging from about 0.01% to about 2.5%, about 0.025% to about 3.0%, about 0.05% to about 1.5%, about 0.07% to about 1.2%, about 0.08% to about 1.4%, about 0.09% to about 2.5%, or about 0.10% to about 2.3%. In certain non-limiting embodiments, glacial acetic acid is present in the oral liquid composition in a w/w concentration of about 0.16% based on the total weight of solids used to prepare to oral liquid composition.

In certain non-limiting embodiments, acid may be incorporated in the oral liquid compositions according to the present disclosure in a concentration sufficient to adjust the pH to a range of about 1.0 to about 5.0, or to any pH or within any pH range subsumed therein. In certain non-limiting embodiments, acid may be included in the oral liquid compositions in a concentration sufficient to adjust the pH of the oral liquid composition to a pH in a range of about 0.5 to about 3.75, about 0.5 to about 5.5, about 0.75 to about 3.0, about 1.0 to about 2.5, about 1.1 to about 5.1, about 1.5 to about 4.5, about 1.0 to about 3.0, about 1.5 to about 2.5, about 2.0 to about 4.0, about 2.0 to about 5.0, about 1.75 to about 5.0, about 1.75 to about 4.5, about 1.75 to about 4.0, about 1.75 to about 3.75, about 2.5 to about 4.0, about 2.75 to about 3.75, about 3.0 to about 3.75, about 3.25 to about 3.75, about 3.0 to about 4.0, or about 1.5 to about 4.0. In certain non-limiting embodiments, acid may be included in the oral liquid compositions in a concentration sufficient to adjust the pH of the oral liquid compositions to a pH of about 2.0 or about 3.5.

In certain non-limiting embodiments of oral liquid compositions according to the present disclosure, glacial acetic acid is included in the oral liquid compositions in a concentration sufficient to provide an unexpectedly highly solubilized composition with surprising and unanticipated stability. In certain non-limiting embodiments, glacial acetic acid is present in the oral liquid composition in a concentration ranging from about 0.0020 mg/mL to about 50 mg/mL based on the total volume of the oral liquid composition, or in any concentration value or concentration range subsumed therein. In certain non-limiting embodiments, glacial acetic acid is present in the oral liquid composition in a concentration ranging from about 0.0010 mg/mL to about 2.0 mg/mL, about 0.0010 mg/mL to about 11 mg/mL, about 0.0010 mg/mL to about 40 mg/mL, about 0.0012 mg/mL to about 0.75 mg/mL, about 0.0012 mg/mL to about 5.0 mg/mL, about 0.0020 mg/mL to about 0.50 mg/mL, about 0.0020 mg/mL to about 12 mg/mL, about 0.0020 mg/mL to about 38 mg/mL, about 0.0020 mg/mL to about 11.0 mg/mL, about 0.005 mg/mL to about 35 mg/mL, about 0.005 mg/mL to about 3.0 mg/mL, about 0.007 mg/mL to about 11 mg/mL, about 0.007 mg/mL to about 11 mg/mL, about 0.007 mg/mL to about 36 mg/mL, about 0.010 mg/mL to about 11 mg/mL, about 0.015 mg/mL to about 33 mg/mL, about 0.020 mg/mL to about 11 mg/mL, about 0.020 mg/mL to about 18 mg/mL, about 0.050 mg/mL to about 10.0 mg/mL, about 0.050 mg/mL to about 20 mg/mL, about 0.075 mg/mL to about 7.0 mg/mL, about 0.075 mg/mL to about 19 mg/mL, about 0.070 mg/mL to about 5.0 mg/mL, about 0.070 mg/mL to about 20 mg/mL, about 0.10 mg/mL to about 4.0 mg/mL, about 0.10 mg/mL to about 20 mg/mL, about 0.12 mg/mL to about 6.0 mg/mL, about 0.12 mg/mL to about 15 mg/mL, about 0.15 mg/mL to about 7.0 mg/mL, about 0.20 mg/mL to about 10.0 mg/mL, about 0.5 mg/mL to about 8.0 mg/mL, about 0.75 mg/mL to about 6.0 mg/mL, about 0.80 mg/mL to about 3.0 mg/mL, about 0.90 mg/mL to about 2.0 mg/mL, or about 1.0 mg/mL to about 5.0 mg/mL, about 1.0 mg/mL to about 10 mg/mL, all based on the total volume of the oral liquid composition. In certain non-limiting embodiments, glacial acetic acid is present in a concentration of about 1.6 mg/mL based on the total volume of the oral liquid composition.

In certain non-limiting embodiments of oral liquid compositions according to the present disclosure, citric acid and/or anhydrous citric acid is included in the oral liquid compositions in a concentration sufficient to provide a composition with surprising and unanticipated stability. In certain non-limiting embodiments, citric acid and/or anhydrous citric acid is present in the oral liquid composition in a total concentration ranging from about 0.5 mg/mL to about 8.0 mg/mL based on the total volume of the oral liquid composition, or in any concentration value or concentration range subsumed therein. In certain non-limiting embodiments, citric acid and/or anhydrous citric acid is present in the oral liquid composition in a total concentration ranging from about 0.6 mg/mL to about 7.5 mg/mL, about 0.75 mg/mL to about 7.0 mg/mL, about 1.0 mg/mL to about 6.5 mg/mL, about 1.5 mg/mL to about 6.0 mg/mL, about 2.0 mg/mL to about 5.5 mg/mL, about 2.4 mg/mL to about 5.1 mg/mL, about 0.5 mg/mL to about 5.0 mg/mL, about 0.75 mg/mL to about 4.0 mg/mL, about 1.0 mg/mL to about 3.5 mg/mL, about 1.5 mg/mL to about 3.0 mg/mL, about 2.0 mg/mL to about 3.0 mg/mL, about 2.25 mg/mL to about 2.75 mg/mL, about 3.0 mg/mL to about 7.0 mg/mL, about 4.0 mg/mL to about 6.5 mg/mL, about 4.0 mg/mL to about 6.0 mg/mL, about 3.5 mg/mL to about 5.5 mg/mL, or about 2.0 mg/mL to about 6.0 mg/mL, all based on the total volume of the oral liquid composition. In certain non-limiting embodiments, citric acid and/or anhydrous citric acid is present in a total concentration of about 2.5 mg/mL based on the total volume of the oral liquid composition. In certain non-limiting embodiments, citric acid and/or anhydrous citric acid is present in a total concentration of about 5.0 mg/mL based on the total volume of the oral liquid composition.

In certain non-limiting embodiments of oral liquid compositions according to the present disclosure, can include one or more preservative compounds to inhibit microbial growth and/or reduce the rate of metabolic deterioration of the carvedilol in the composition, increasing composition stability. In certain non-limiting embodiments, the preservative may be one or more compounds selected from sodium benzoate, antimol, benzoic acid, carboxybenzene sodium salt, benzoan sodny, benzalkonium chloride, cetrimonium bromide, benzethonium chloride, alkyltrimethylammonium bromide, benzalkonium chloride/edetic acid, edetic acid, amino aryl acid esters, phenol, methylparaben, ethylparaben, propylparaben, butylparaben, chlorobutanol, phenylmercuric nitrate, sorbic acid, potassium sorbate, chlorocresol, glycerol, benzyl alcohol, cetyl alcohol, stearyl alcohol, sorbic acid, chloroactamide, trichlorocarban, thimerosal, imidurea, bronopol, chlorhexidine, 4-chlorocresol, 4-chloroxylenol, dichlorophene, and hexachlorophene.

In certain non-limiting embodiments, oral liquid compositions according to the present disclosure include sodium benzoate as a preservative. In certain non-limiting embodiments, the oral liquid compositions include about 0.05%, by weight, of sodium benzoate or another preservative. In certain non-limiting embodiments, the sodium benzoate concentration in the oral liquid composition is greater than 0 and less than about 5%, by weight, or is at any concentration value or in any concentration range subsumed therein, such as, for example, 4% w/w, 3% w/w, 2% w/w, 1% w/w, greater than 0 to less than about 1% w/w, about 0.001% w/w to about 0.10% w/w, about 0.005% w/w to about 0.07% w/w, or about 0.01% w/w to about 0.10% w/w. In certain non-limiting embodiments according to the present disclosure, the oral liquid compositions herein may include sodium benzoate in a concentration of about 0.05% w/w, based on the total weight of the oral liquid composition.

In certain non-limiting embodiments the oral liquid compositions according to the present disclosure include about 0.005 mg/mL to about 5.0 mg/mL of sodium benzoate or another preservative such as methyl paraben or propyl paraben, based on the total volume of the oral liquid composition, or in any concentration value or concentration range subsumed therein. In certain non-limiting embodiments, the sodium benzoate concentration in the oral liquid compositions herein is greater than 0 and less than about 1.5 mg/mL, or sodium benzoate is present at any value or in any range subsumed therein, such as, for example, greater than 0 to less than about 1.5 mg/mL, about 0.001 mg/mL to about 1.25 mg/mL, about 0.007 mg/mL to about 1.5 mg/mL, about 0.01 mg/mL to about 1.0 mg/mL, about 0.5 mg/mL to about 5 mg/mL, about 1.0 mg/mL to about 4.0 mg/mL, about 1.5 mg/mL to about 3.0 mg/mL, about 0.5 mg/mL to about 3.5 mg/mL, or about 1.0 mg/mL to about 3.0 mg/mL. In certain non-limiting embodiments according to the present disclosure, the oral liquid compositions disclosed herein may include sodium benzoate in a concentration of about 0.5 mg/mL, based on the total volume of the oral liquid composition. In certain non-limiting embodiments according to the present disclosure, the oral liquid compositions disclosed herein may include methyl paraben in a concentration of about 2.0 mg/mL, based on the total volume of the oral liquid composition. In certain non-limiting embodiments according to the present disclosure, the oral liquid compositions disclosed herein may include propyl paraben in a concentration of about 0.20 mg/mL, based on the total volume of the oral liquid composition.

In certain non-limiting embodiments, oral liquid compositions according to the present disclosure can comprise one or more additional excipients including, but not limited to, sweeteners, flavoring agents, stabilizers, coloring agents, thickeners, and the like. Excipients can be selected based on function and compatibility with the oral liquid compositions disclosed herein and various such possible excipients may be found, for example, in Kibbe, Arthur H., "Handbook of Pharmaceutical Excipients", 6th ed. (London, Pharmaceutical Press, 2009), which is hereby incorporated by reference herein in its entirety.

One or more sweeteners or sweetening agents can be used in the oral liquid composition and can include any compounds that provide a sweet taste, including, for example, natural and synthetic sugars, natural and artificial sweeteners, natural extracts and any material that initiates a sweet sensation in a subject. In some embodiments, the oral liquid composition disclosed herein comprises one or more sweeteners. In some embodiments, solid, powder sweeteners are used in the liquid composition disclosed herein. In other embodiments, sweeteners in liquid form, also referred to as syrups, are used in the oral liquid composition disclosed herein.

Suitable sweeteners for inclusion in the oral liquid composition include, but are not limited to, glucose, fructose, sucrose, xylitol, tagatose, sucralose, maltitol, isomaltulose, ISOMALT™ (hydrogenated isomaltulose), lactitol, sorbitol, mannitol, erythritol, trehalose, maltodextrin, polydextrose, and the like. Other sweeteners that may be included in the compositions herein include, for example, glycerin, inulin, erythritol, maltol, acesulfame and salts thereof (e.g., acesulfame potassium), alitame, aspartame, neotame, sodium cyclamate, saccharin and salts thereof (e.g., saccharin sodium or saccharin calcium), neohesperidin dihydrochalcone, stevioside, thaumatin, and the like. Sweeteners can be used in the form of crude or refined products, such as, for example, hydrogenated starch hydrolysates, maltitol syrup, or high fructose corn syrup, and as branded products, e.g., SWEET AM™ liquid (Product Code 918.003—propylene glycol, ethyl alcohol, and proprietary artificial flavor combination, Flavors of North America), SWEET AM™ powder (Product Code 918.005—maltodextrin, sorbitol, and fructose combination and Product Code 918.010—water, propylene glycol, sorbitol, fructose, and proprietary natural and artificial flavor combination, Flavors of North America), PROSWEET™ (1-10% proprietary plant/vegetable extract and 90-99% dextrose combination, Virginia Dare), MALTISWEET™ (maltitol solution, Ingredion) and SORBO™ (sorbitol and sorbitol/xylitol solution, SPI Polyols), INVERTOSE™ (high fructose corn syrup, Ingredion), and ORA-SWEET™ sugar-free flavored syrup (Paddock Laboratories, Inc.). Sweeteners can be used singly or in combinations of two or more. In some embodiments, the sweetener is sucralose. Suitable concentrations of different sweeteners can be selected based on published information, manufacturers' data sheets, and/or by routine testing.

In certain non-limiting embodiments according to the present disclosure, the oral liquid composition disclosed herein may include sweetener in a concentration ranging from about 4.0 mg/mL to about 10.0 mg/mL, based on the total volume of the oral liquid composition, or in any concentration value or concentration range subsumed therein. In certain non-limiting embodiments, sweetener is present in the oral liquid composition in a concentration ranging from about 1.5 mg/mL to about 12 mg/mL, about 2.0 mg/mL to about 11 mg/mL, about 3.0 mg/mL to about 10 mg/mL, about 3.5 mg/mL to about 10.5 mg/mL, about 4.0 mg/mL to about 9.0 mg/mL, about 4.5 mg/mL to about 8.5 mg/mL, about 5.0 mg/mL to about 10 mg/mL, about 5.5 mg/mL to about 8.0 mg/mL, about 6.0 mg/mL to about 7.5 mg/mL, about 5.5 mg/mL to about 9 mg/mL, about 6.0 mg/mL to about 10 mg/mL, about 4.5 mg/mL to about 7.5 mg/mL, or about 6.5 mg/mL to about 7.5 mg/mL. In certain non-limiting embodiments according to the present disclosure, the oral liquid compositions disclosed herein may include sweetener in a concentration of about 6.8 mg/mL, based on the total volume of the oral liquid composition. In certain non-limiting embodiments according to the present disclosure, the oral liquid compositions disclosed herein may include sweetener in a concentration of about 5.0 mg/mL, based on the total volume of the oral liquid composition.

In certain non-limiting embodiments according to the present disclosure, the oral liquid composition disclosed herein may include sweetener in a concentration ranging from about 0.01% w/w to about 3.0% w/w, based on the total weight of the oral liquid composition, or in any concentration value or concentration range subsumed therein. In certain non-limiting embodiments, a sweetener is present in the oral liquid composition in a concentration ranging from about 0.05% w/w to about 2.5% w/w, about 0.1% w/w to about 2.0% w/w, about 0.4% w/w to about 1.5% w/w, about 0.3% w/w to about 1.25% w/w, about 0.5% w/w to about 0.75% w/w, or about 0.4% w/w to about 0.75% w/w, all based on the total weight of the oral liquid composition. In certain non-limiting embodiments according to the present disclosure, the oral liquid compositions disclosed herein may include sweetener in a concentration of about 0.68% w/w, based on the total weight of the oral composition. In certain non-limiting embodiments according to the present disclosure, the oral liquid compositions disclosed herein may include sweetener in a concentration of about 0.50% w/w, based on the total weight of the oral composition.

One or more flavoring agents can be used to enhance the taste or aroma of the oral liquid composition. Suitable natural or synthetic flavoring agents can be selected from standard reference books, for example, Fenaroli's Handbook of Flavor Ingredients, 3rd edition (1995). Non-limiting examples of suitable natural flavors for inclusion in the oral liquid composition, some of which can readily be simulated with synthetic agents or combinations thereof, include almond, anise, apple, apricot, bergamot, blackberry, blackcurrant, blueberry, cacao, caramel, cherry, cinnamon, clove, coffee, coriander, cranberry, cumin, dill, eucalyptus, fennel, fig, ginger, grape, grapefruit, guava, hop, lemon, licorice, lime, malt, mandarin, molasses, nutmeg, orange, peach, pear, peppermint, peppermint oil, pineapple, raspberry, rose, spearmint, strawberry, tangerine, tea, tutti-frutti, vanilla, wintergreen, and the like. In certain embodiments, flavoring agents include cherry, grape, and bubblegum. In some embodiments, the liquid composition comprises a grape flavoring agent.

In certain non-limiting embodiments according to the present disclosure, the oral liquid composition disclosed herein may include one or more flavoring agents in a concentration ranging from about 0.005 mg/mL to about 5.0 mg/mL, based on the total volume of the oral liquid composition, or in any concentration value or concentration range subsumed therein. In certain non-limiting embodiments, flavoring agent is present in the oral liquid compositions in a concentration ranging from about 0.01 mg/mL to about 4.0 mg/mL, about 0.025 mg/mL to about 3.0 mg/mL, about 0.05 mg/mL to about 2.5 mg/mL, about 0.10 mg/mL to about 2.0 mg/mL, about 0.5 mg/mL to about 2.5 mg/mL, about 0.75 mg/mL to about 1.5 mg/mL, about 0.6 mg/mL to about 1.75 mg/mL, about 45 mg/mL to about 75 mg/mL, about 50 mg/mL to about 70 mg/mL, about 55 mg/mL to about 65 mg/mL, about 50 to about 63 mg/mL, or about 55 mg/mL to about 60 mg/mL. In certain non-limiting embodiments according to the present disclosure, the oral liquid compositions disclosed herein may include a flavoring agent in a concentration of 1.0 mg/mL, based on the total volume of the oral liquid composition.

In certain non-limiting embodiments according to the present disclosure, the oral liquid compositions disclosed herein may include one or more flavoring agents in a concentration ranging from about 0.001% w/w to about 8.0% w/w, based on the total weight of the oral liquid composition, or in any concentration value or concentration range subsumed therein. In certain non-limiting embodiments, a flavoring agent is present in the oral liquid compositions in a concentration ranging from about 0.01% to about 2.5%, about 0.025% to about 3.0%, about 0.05% to about 1.5%, about 0.07% to about 1.2%, about 0.08% to about 1.4%, about 0.09% to about 2.5%, about 0.10% to about 2.3%, about 2.0% to about 10.0%, about 3.0% to about 9.0%, about 4.0% to about 8.0%, about 3.0% to about 7.0%, 5.0% to about 7.0%, about 5.1% to about 6.5%, or about 4.0% to about 7.0%. In certain non-limiting embodiments, a flavoring agent is present in the oral liquid compositions in a w/w concentration of about 0.10% based on the total weight of the oral liquid composition. In certain non-limiting embodiments according to the present disclosure, the oral liquid compositions disclosed herein may include a flavoring agent in a concentration of 0.10% w/w, based on the total weight of the oral liquid composition. In certain non-limiting embodiments according to the present disclosure, the oral liquid compositions disclosed herein may include a flavoring agent in a concentration of 5.8% w/w.

Coloring agents can be included in embodiments of the oral liquid composition herein for identification and/or aesthetic purposes. Suitable coloring agents include, but are not limited to, FD&C Red No. 3, FD&C Red No. 20, FD&C Red No. 40, FD&C Yellow No. 6, FD&C Blue No. 2, D&C Green No. 5, D&C Orange No. 5, caramel, ferric oxide, and mixtures thereof.

The oral liquid compositions disclosed herein may be prepared in the forms of, for example and without limitation, aqueous solutions, nonaqueous solutions, juices, elixirs, and the like. Despite carvedilol having low solubility, embodiments of the oral liquid compositions herein surprisingly are solutions rather than suspensions, and no active ingredient is present as particulate matter or in a solid form in the compositions. Fully solubilizing the active ingredients, such as carvedilol, in the oral liquid compositions herein provides advantages over their partially solubilized counterparts (e.g., suspensions, slurries, etc.). Such advantages include, for example, higher drug absorption and drug permeability, leading to improved bioavailability. However, low solubility active ingredients, such as carvedilol, typically pose significant challenges to formulating liquid compositions in which the active ingredient is completely solubilized and remains in solution until administration. The oral liquid compositions disclosed herein overcome those challenges.

Suitable liquid vehicles for use in the oral liquid compositions herein may be selected based on imparting desired qualities including, for example, clarity, nontoxicity, acceptable viscosity, compatibility with excipients, chemical inertness, palatability, acceptable odor and color, and/or economy. Examples of liquid vehicles that may be used include, for example, water, ethyl alcohol, glycerin, polyethylene glycol 400 (PEG 400), propylene glycol, syrup (sugar or other sweetener based substance, e.g., ORA-SWEET® SF sugar-free flavored syrup), juices (apple, grape, orange, cranberry, cherry, tomato, and the like), other beverages (tea, coffee, soft drinks, milk, and the like), oils (olive, soybean, corn, mineral, castor, and the like), and combinations or mixtures thereof. In various embodiments, certain liquid vehicles, e.g., one or more oils and water, can be combined to form emulsions for inclusion in the oral liquid composition. In certain non-limiting embodiments, water is used as a vehicle in the oral liquid composition. In certain non-limiting embodiments, a syrup is used as a vehicle in the oral liquid composition. In various non-limiting embodiments, a juice is used as a vehicle in the oral liquid composition.

In certain non-limiting embodiments according to the present disclosure, the oral liquid composition disclosed herein is a homogeneous liquid. As used herein, a "homogeneous liquid" refers to a liquid that is substantially uniform in appearance, identity, consistency, and drug concentration per volume. Non-homogeneous liquids include liquids that have varied coloring and/or viscosity, as well as non-uniform drug concentration in unit volume. Homogeneity in liquids is assessed by qualitative identification or appearance tests and/or quantitative High Performance Liquid Chromatography (HPLC) testing or the like. Exemplary qualitative testing includes visual inspection of the resultant liquid for air bubbles and/or undissolved solids which may cause variable dosing. Analytical HPLC testing can also determine drug concentration uniformity by examining aliquots of certain volume sections (e.g., 5 or 10 mL from the top, middle, and bottom of a 150 mL bottle). The mixing methods and excipients disclosed herein are selected to impart a homogeneous quality to the oral liquid composition.

Mixing methods encompass any type of mixing resulting in a homogeneous oral liquid composition. Mixing can include, for example, one or more of stirring, shaking, swirling, agitating, and inverting. In certain non-limiting embodiments, individual components of the oral liquid composition are added sequentially, concurrently, or in any combination thereof to a liquid vehicle. In certain non-limiting embodiments, individual components are added sequentially, one at a time. In certain non-limiting embodiments, the sequential addition of individual components includes mixing for a certain time interval after each or some of the sequential additions. In various non-limiting embodiments, all individual components are added at the same time to a liquid vehicle and are then mixed for a certain time interval. In various non-limiting embodiments disclosed herein, mixing occurs for certain time intervals, such as, for example, the individual components of the oral liquid composition are mixed for a time period sufficient to produce a homogeneous liquid. The oral liquid compositions herein are stable under various storage conditions, including refrigerated and ambient conditions. As used herein, the term "stable" refers to the characteristic that the oral liquid composition retains at least about 90% of the initial carvedilol amount, retains at least about 95% of the initial carvedilol amount, or retains at least about 98% of the initial carvedilol amount at the end of a given storage period under specified storage conditions. The term "stable" can also refer to an oral liquid composition including about 1% w/w or less total impurities or related substances, about 0.5% w/w or less total impurities or related substances, or about 0.4% w/w or less total impurities or related substances at the end of a given storage period under specified storage conditions. The term "stable" can also refer to an oral liquid composition including about 0.5% w/w or less individual impurities or related substances, or about 0.2% w/w or less individual impurities or related substances at the end of a given storage period under specified storage conditions. The term "stable" can also refer to an oral liquid composition including less than about $10^2$ total aerobic microbial count at the end of a given storage period under specified storage conditions. The term "stable" can also refer to an oral liquid composition including less than about $10^1$ total combined yeast and mold count at the end of a given storage period under specified storage conditions. The term "stable" can also refer to the absence or non-detection of Escherichia coli and/or Burkholderia cepacia within the oral liquid composition following a given storage period under specified storage conditions.

In certain non-limiting embodiments, the oral liquid compositions according to the present disclosure are stable under refrigerated (5° C.±3° C.) and standard conditions (25° C.±2° C. and 40%±5% relative humidity) on storage under those conditions for a period ranging from about 2 weeks to about 3.5 years, about 1 month to about 36 months, about 1 month to about 30 months, about 1 month to about 24 months, about 1 month to about 18 months, about 1 month to about 12 months, about 1 month to about 9 months, about 1 month to about 6 months, about 1 month to about 4 months, about 1 month to about 3 months, about 2 months to about 24 months, about 2 months to about 18 months, about 2 months to about 12 months, about 2 months to about 9 months, about 2 months to about 6 months, about 2 months to about 4 months, about 2 months to about 3 months, about 3 months to about 24 months, about 3 months to about 18 months, about 3 months to about 12 months, about 3 months to about 9 months, about 3 months to about 6 months, about 4 months to about 24 months, about 4 months to about 18 months, about 4 months to about 9 months, or about 4 months to about 6 months. In certain embodiments, the oral liquid compositions herein are stable under refrigerated (5° C.±3° C.) and standard conditions (25° C.±2° C. and 40%±5% RH) for up to 12 weeks, up to 16 weeks, up to 20 weeks, up to 24 weeks, up to 28 weeks, up to 32 weeks, up to 36 weeks, up to 48 weeks, up to 52 weeks, up to 60 weeks, up to 72 weeks, up to 84 weeks, up to 96 weeks, up to 104 weeks, up to 108 weeks or up to 120 weeks.

Standard conditions, also referred to as controlled room temperature (CRT) conditions, include temperature and/or relative humidity (RH) that are at standard conditions (e.g., 25° C.±2° C. and 40%±5% RH). In some instances, standard conditions include temperatures of about 20° C., about 21° C., about 22° C., about 23° C., about 24° C., about 25° C., about 26° C., about 27° C., about 28° C., about 29° C., or about 30° C. In certain embodiments, standard conditions include 40%±5% relative humidity and a temperature range of, for example, about 23° C. to about 27° C., about 22° C. to about 28° C., or about 24° C. to about 26° C. In certain embodiments, standard conditions include a temperature of 25° C.±2° C. and a relative humidity range of, for example, about 37% to about 42%, about 34% to about 47%, or about 36% to about 46%. In other instances, standard conditions include a relative humidity of about 45% RH, about 50% RH, about 55% RH, about 60% RH, or about 65% RH.

Refrigerated conditions include temperatures and/or relative humidities conventional in typical refrigeration units. Such conventional temperatures include, for example, 5±3° C. In certain non-limiting embodiments, refrigerated conditions include a temperature of, for example, about 1° C. to about 10° C., about 2° C. to about 9° C., about 3° C. to about 8° C., or about 1° C. to about 8° C. In some instances, refrigerated conditions include about 2° C., about 3° C., about 4° C., about 5° C., about 6° C., about 7° C., or about 8° C.

Intermediate conditions (e.g., 30±2° C. and 65%±5% RH) include temperatures in a range that is between the temperatures for standard conditions (e.g., 25±2° C.) and accelerated conditions (e.g., 40±2° C.). In certain non-limiting embodiments, intermediate conditions include a relative humidity of 65%±5% relative humidity and a temperature, for example, of about 26° C. to about 34° C., about 27° C. to about 33° C., about 28° C. to about 32° C., about 29° C. to about 31° C., about 29° C. to about 33° C., or about 28° C. to about 34° C.

Accelerated conditions (e.g., 40±2° C. and no more than (NMT) 25% RH) include temperatures higher than those under intermediate conditions (e.g., 30±2° C.). In certain non-limiting embodiments, accelerated conditions include no more than 25% relative humidity and a temperature range of, for example, about 38° C. to about 42° C., about 39° C. to about 43° C., or about 39° C. to about 45° C. In certain non-limiting embodiments, accelerated conditions include about 10% to about 40%, about 15% to about 35%, or about 20% to about 30% relative humidity.

Methods of Treatment:

Another aspect of the present disclosure provides methods of treatment comprising administering an oral liquid composition according to the present disclosure to a subject in need thereof. In certain non-limiting embodiments of such methods, an oral liquid composition herein can be used to treat hypertension in a subject. Hypertension, as used herein, includes both primary (essential) hypertension and secondary hypertension. Hypertension can be classified in cases when blood pressure values are greater than or equal to 140/90 (systolic/diastolic) mm Hg in an adult subject. In non-limiting embodiments of the methods herein, an oral liquid composition according to the present disclosure is administered to treat primary (essential) hypertension in a subject. In other non-limiting embodiments of the methods herein, an oral liquid composition according to the present disclosure is administered to treat secondary hypertension in a subject. In certain non-limiting embodiments, the subject is a geriatric subject. Hypertension in geriatric patients is defined similarly to that in adult patients, i.e., blood pressure values greater than or equal to 140/90 (systolic/diastolic) mm Hg.

In certain non-limiting embodiments of the methods according to the present disclosure, an oral liquid composition according to the present disclosure can be used to treat heart failure. In certain non-limiting embodiments of the methods herein, an oral liquid composition according to the present disclosure can be used to reduce cardiovascular mortality in clinically stable patients with left ventricular failure or left ventricular dysfunction following myocardial infarction.

Dosing:

In one aspect, the oral liquid compositions herein are used for the treatment of diseases and conditions disclosed herein. In addition, a method for treating any of the diseases or conditions disclosed herein in a subject in need of such treatment involves administering to the subject a therapeutically effective amount of an oral liquid composition according to the present disclosure.

Dosages of the oral liquid compositions disclosed herein that should be administered to subjects in need thereof can be determined by any suitable method. Maximum tolerated dose (MTD) and maximum response dose (MRD) for carvedilol can be determined via established animal and human experimental protocols. For example, toxicity and therapeutic efficacy of carvedilol can be determined by standard pharmaceutical procedures in cell cultures or experimental animals, including, but not limited to, determination of the $LD_{50}$ (the dose lethal to 50% of the population) and the $ED_{50}$ (the dose therapeutically effective in 50% of the population). The dose ratio between the toxic and therapeutic effects is known as the therapeutic index, and it can be expressed as a ratio between $LD_{50}$ and $ED_{50}$. Carvedilol dosages exhibiting high therapeutic indices are desirable. The data obtained from cell culture assays and animal studies can be used in formulating a range of dosage for use in humans. An $LD_{Lo}$ value is the lowest amount of a solid or liquid material reported to have caused the death of animals or humans. For example, in animal subjects toxicity of carvedilol is reported as an oral $LD_{LO}$ for rats of 8 gm/kg; the intraperitoneal $LD_{50}$ for rats is 769 mg/kg; the oral $LD_{LO}$ for mice is 8 gm/kg; the intraperitoneal $LD_{50}$ in mice is 364 mg/kg. In humans, toxicity of carvedilol is reported as a toxic dose low ($TD_{LO}$) or the lowest dose of a substance introduced by any route, other than inhalation, over any given period of time, and reported to produce any toxic effect in humans or to produce tumorigenic or reproductive effects in animals. For example, the toxicity of carvedilol is reported as an oral $TD_{LO}$ for men of 5.357 mg/kg and an oral $TD_{LO}$ for women of 12 mg/kg. The dosage of such compounds lies preferably within a range of circulating concentrations that include the $ED_{50}$ with minimal toxicity. The dosage may vary within this range depending upon the dosage form employed and the route of administration utilized. Additional relative dosages, represented as a percent of maximal response or of maximum tolerated dose, are readily obtained via these protocols.

In certain non-limiting embodiments, the dose of carvedilol in the oral liquid composition administered to a subject for treating adult hypertension is provided in a dosing schedule. For example, in various embodiments of a method for treating adult hypertension according to the present disclosure, the dosing schedule for treating adult hypertension begins with about 6.25 mg of carvedilol in the oral liquid composition twice daily and increasing, if needed for blood pressure control, to about 12.5 mg, and then to no more than 25.0 mg administered twice daily, with food, over intervals of one to two weeks. In certain embodiments of a method for treating adult hypertension, carvedilol in the oral liquid composition can be administered over a dose range of 2.0 mg to 25 mg, 3.0 mg to 25 mg, 4.0 mg to 25 mg, 5.0 mg to 25 mg, 5.5 mg to 25 mg, 6.0 mg to 25 mg, 9.0 mg to 25 mg, or 10.0 mg to 25 mg, administered twice a day.

In certain embodiments, the dose of carvedilol in the oral liquid composition administered to a subject for treating hypertension or post-myocardial infarction in geriatric patients is up to 50 mg of carvedilol in the oral liquid composition once daily. In certain embodiments of a method for treating adult hypertension in geriatric patients, carvedilol in the oral liquid composition can be administered over a dose range of 30 mg to 50 mg, 35 mg to 50 mg, 40 mg to 50 mg, 45 mg to 50 mg, 47 mg to 50 mg, or 48 mg to 50 mg, administered once a day.

In certain embodiments, the dose of carvedilol in the oral liquid composition administered to a subject for treating adult heart failure is provided in a dosing schedule. For example, in various embodiments of a method for treating adult heart failure according to the present disclosure, the dosing schedule for treating adult heart failure begins with about 3.125 mg of carvedilol in the oral liquid composition twice daily and increasing to a maximum of 25 mg administered twice daily, with food, over intervals of at least two weeks. Depending on the tolerance of the patient to the treatment, lower doses of the carvedilol in the oral liquid composition may be maintained if the higher doses are not well tolerated.

In certain embodiments, the dose of carvedilol in the oral liquid composition administered to a subject for treating adult heart failure is 3.125 mg to 25 mg, administered twice daily in an oral liquid composition according to the present disclosure. For example, the dose of carvedilol for treating adult heart failure in an oral liquid composition according to the present disclosure may be about 3.125 mg, about 6.25 mg, about 12.5 mg, or up to 25 mg, wherein the dose is administered twice daily. In various embodiments of methods for treating adult heart failure according to the present disclosure, carvedilol in an oral liquid composition according to the present disclosure can be administered to a subject over a dose range from 2.0 mg to 25 mg, 2.5 mg to 25 mg, 3.0 mg to 25 mg, 4.0 to 25 mg, 4.0 to 25 mg, 5.0 to 25 mg, 5.5 mg to 25 mg, 6.0 mg to 25 mg, or 9.0 mg to 25 mg, wherein the dose is administered twice a day.

In certain embodiments, the dose of carvedilol in the oral liquid composition administered to a subject for treating heart failure in geriatric patients is 50 mg of carvedilol in the oral liquid composition once daily.

In certain embodiments, the dose of carvedilol in the oral liquid composition administered to a subject for treating left ventricular dysfunction following myocardial infarction is provided in a dosing schedule. For example, in various embodiments of a method for treating left ventricular dysfunction according to the present disclosure, the dosing schedule for treating left ventricular dysfunction begins with 3.125 mg of carvedilol in the oral liquid composition twice daily and increasing, as needed, to no more than 25.0 mg administered twice daily, with food, over intervals of three to ten days. Depending on the tolerance of the patient to the treatment, lower starting doses of the carvedilol in the oral liquid composition and/or slower titration may be used if the higher doses are not well tolerated.

In certain non-limiting embodiments of methods according to the present disclosure, an oral liquid composition according to the present disclosure including carvedilol can be administered to an adult for treating left ventricular dysfunction following myocardial infarction. For example, in various non-limiting embodiments of such methods, an oral liquid composition according to the present disclosure can be administered to a subject to provide a carvedilol dose in a range of 3.1 mg to 25 mg, wherein the dose is administered twice daily. In certain non-limiting embodiments of methods for treating left ventricular dysfunction in adults according the present disclosure, an oral liquid composition according to the present disclosure can be administered to a subject to provide a dose of carvedilol in a range of 2.5 mg to 25 mg, 3.0 mg to 25 mg, 1.0 mg to 25 mg, or 2.0 mg to 25 mg, wherein the dose is administered twice daily.

Administration:

Oral liquid compositions according to the present disclosure can be administered at a dosage disclosed herein or at other appropriate dose levels contemplated by a medical practitioner. In certain non-limiting embodiments, the oral liquid compositions according to the present disclosure are administered for prophylactic and/or therapeutic treatments. In certain therapeutic applications, the oral liquid compositions are administered to a patient already suffering from an indication, e.g., hypertension, in a therapeutically effective amount sufficient to cure the disease or at least partially arrest or ameliorate the symptoms, e.g., lower blood pressure. Amounts effective for this use depend on, for example, the age of the patient, severity of the disease, previous therapy, the patient's health status, weight, and response to the oral liquid compositions, and determining an effective amount is within the judgment of the treating physician. Therapeutically effective amounts are optionally determined by methods including, but not limited to, a dose escalation clinical trial.

In certain embodiments wherein the patient's condition does not improve, upon the doctor's discretion, the oral liquid composition disclosed herein may be administered chronically, that is, for an extended period of time, including throughout the duration of the patient's life, to ameliorate or otherwise control or limit the symptoms of the patient's disease. In certain non-limiting embodiments, administration of the oral liquid composition continues until complete or partial response of a disease occurs.

EXAMPLES

Example 1. Preparation of an Oral Liquid Composition Including Carvedilol

An oral liquid composition was prepared using the method described below. Table 2 shows the composition of the oral liquid composition, RD0013-067, including 1.25 mg/mL of carvedilol, 10 mg/mL of hydroxypropyl beta-cyclodextrin, and 1.6 mg/mL of glacial acetic acid, with a balance of purified water.

TABLE 2

Composition of oral liquid composition RD0013-067 including 1.25 mg/mL of carvedilol (0.125% by weight) at pH 3.5.

| Ingredient | % w/w | mg/mL | mg/5 mL | mg/10 mL | mg/20 mL | mg/40 mL | mg/80 mL |
|---|---|---|---|---|---|---|---|
| Carvedilol | 0.125 | 1.25 | 6.25 | 12.5 | 25 | 50 | 100 |
| Hydroxypropyl β-cyclodextrin | 1.00 | 10.0 | 50.0 | 100 | 200 | 400 | 800 |
| Glacial acetic acid | 0.16 | 1.60 | 8.00 | 16.0 | 32.0 | 64.0 | 128 |
| Purified water | 98.7 | 987 | 4936 | 9872 | 19743 | 39486 | 78972 |
| Total | 100 | 1000 | 5000 | 10000 | 20000 | 40000 | 80000 |

Unless otherwise noted, all components were added in the quantities/concentrations provided in Table 2 and steps were performed at standard testing conditions of no more than (NMT) 30° C. and NMT 85% relative humidity. Initially, the purified water and the hydroxypropyl β-cyclodextrin were mixed with stirring and the pH of the water/hydroxypropyl β-cyclodextrin mixture was adjusted to a target pH of 3.5 to 4.0 using glacial acetic acid to form a first mixture. Next, the carvedilol was added to the first mixture with stirring and again the pH of the mixture was adjusted to a target pH of 3.5 to 4.0 using the glacial acetic acid to form a second mixture. Finally, the remaining purified water (quantum satis) was added to the second mixture with stirring to form the oral liquid composition RD0013-067 of Table 2. The pH of the final composition was pH was 3.9.

Example 2

A study was conducted to assess the stability of the oral liquid composition, RD0013-067, prepared in Example 1 including 1.25 mg/mL of carvedilol, 10 mg/mL of hydroxypropyl beta-cyclodextrin, and 1.6 mg/mL of glacial acetic acid.

Figure 3A:
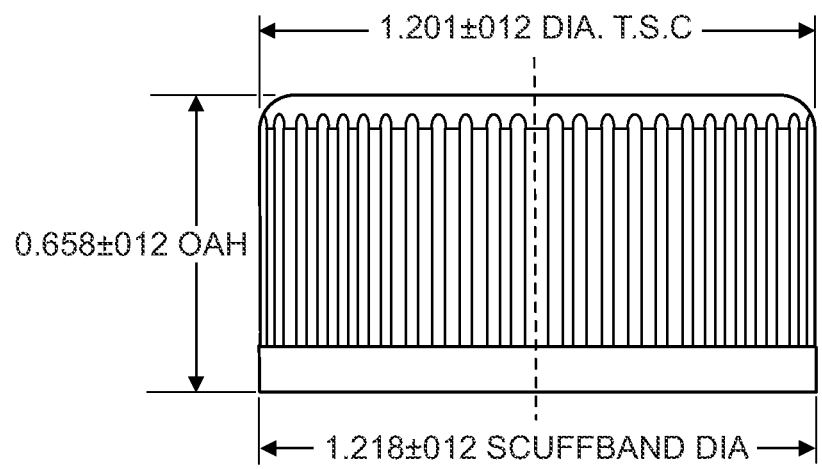
Figure 3B:
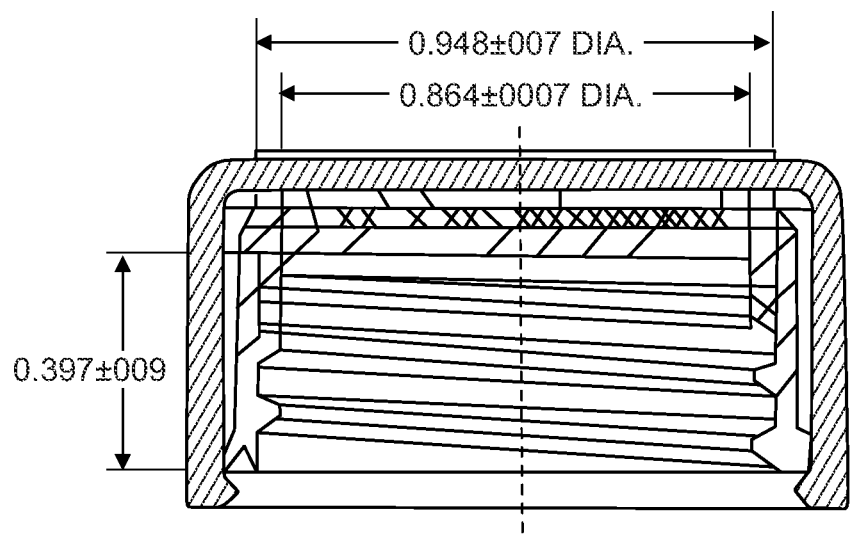

For purposes of conducting a stability study, 120 mL of the oral liquid composition RD0013-067 was packaged in a container closure system. Each container closure system, as shown in FIGS. 2A, 2B, 3A, and 3B, included a 4 ounce (120 mL) Modern Boston Round Amber (colorant: 66N4452 Amber), LASER+™ C (C60A) (resin: polyethylene terephthalate) bottle (see FIGS. 2A and 2B) with a 24 mm SECURX™ ribbed side pictorial top (resin: INEOS H20E-00), a white closure (colorant: white 11343 AMPACET), with a foam liner (liner: SELIG SEALING 0.035" C25FSLE5-9), as shown in FIGS. 3A and 3B.

Four studies were conducted to assess the stability of the oral liquid composition, RD0013-067, stored in the container closure system. The stability studies involved the following testing periods and conditions:

Standard testing conditions (25° C.±2° C. and 40%±5% RH) for up to 18 months.
Refrigerated testing conditions (5° C.±3° C.) for up to 9 months.
Intermediate testing conditions (30° C.±2° C. and 65%±5% RH) for up to 9 months.
Accelerated testing conditions (40° C.±2° C. and no more than (NMT) 25% RH) for up to 6 months.

A stability study of the oral liquid composition contained in the container closure system and stored under standard testing conditions was conducted over a period of eighteen months to determine the rate of physical or chemical degradation of the 1.25 mg of carvedilol originally included in each mL of the oral liquid composition, RD0013-067.

All standard testing conditions stability samples (each sample consisting of a container closure system containing 120 mL of the oral liquid composition, each mL originally including 1.25 mg/mL of carvedilol) were placed upright in an stability chamber and maintained in an upright position during the stability study. All of the containers were maintained at 25° C.±2° C. and 40%±5% relative humidity conditions, uninterrupted, (except for the addition or withdrawal of test samples) for a period of one, two, three, six, nine, twelve, or eighteen months. Samples were removed from conditions at the specified time points and tested for carvedilol content. Storage of the stability samples was completed using a calibrated stability chamber. Testing of the stability samples was completed using High Performance Liquid Chromatography.

Based on the eighteen month term stability assay results shown in Table 3 for the oral liquid composition, RD0013-067, the shelf life of the oral liquid composition contained in the container closure system was estimated to be at least eighteen months under the standard testing conditions. The stability assay showed that 100 percent of the original carvedilol was retained in the oral liquid composition in the 120 mL bottle over the course of storage at the standard testing conditions for eighteen months.

Table 3 reports stability data for the oral liquid composition, RD0013-067, including 1.25 mg/mL of carvedilol, stored under refrigerated, standard, intermediate, and accelerated testing conditions. In Table 3, $T_0$ refers to time zero.

Table 3. Stability results for the oral liquid composition, RD0013-067, including 1.25 mg/mL carvedilol, in 120 mL bottles stored under refrigerated, standard, intermediate, and accelerated testing conditions over a period of 1, 2, 3, 6, 9, 12, or 18 months.

TABLE 3

Stability results for the oral liquid composition, RD0013-067, including 1.25 mg/mL carvedilol, in 120 mL bottles stored under refrigerated, standard, intermediate, and accelerated testing conditions over a period of 1, 2, 3, 6, 9, 12, or 18 months.

| Time Period | Testing Conditions | Assay Carvedilol % |
| --- | --- | --- |
| $T_0$ | N/A | 106.5 |
| 1 Month | 5° C. ± 3° C. | 99.2 |
| 1 Month | 25° C./40% RH | 101.7 |
| 1 Month | 30° C./65% RH | 100.4 |
| 1 Month | 40° C./NMT 25% RH | 101.6 |
| 2 Months | 40° C./NMT 25% RH | 103.4 |
| 3 Months | 5° C. ± 3° C. | 100.4 |
| 3 Months | 25° C./40% RH | 103.0 |
| 3 Months | 30° C./65% RH | 103.1 |
| 3 Months | 40° C./NMT 25% RH | 92.7 |
| 6 Months | 5° C. ± 3° C. | 96.0 |
| 6 Months | 25° C./40% RH | 103.4 |
| 6 Months | 30° C./65% RH | 102.5 |
| 6 Months | 40° C./NMT 25% RH | 103.5 |
| 9 Months | 5° C. ± 3° C. | 103.7 |
| 9 Months | 25° C./40% RH | 102.6 |
| 9 Months | 30° C./65% RH | 95.4 |
| 12 Months | 5° C. ± 3° C. | 105.2 |
| 12 Months | 25° C./40% RH | 105.3 |
| 12 Months | 30° C./65% RH | 104.7 |
| 18 Months | 25° C./40% RH | 106.1 |

As indicated in Table 3, a stability study of the same oral liquid composition, RD0013-067, was conducted over certain periods (one, three, six, nine, or twelve months) to determine the rate of physical or chemical degradation of the carvedilol in the oral liquid composition in the container closure system stored under refrigerated testing conditions.

All stability samples (each sample comprising a container closure system including 120 mL of the oral liquid composition originally including 1.25 mg/mL of carvedilol) subjected to the refrigerated testing conditions were placed upright in an environmental chamber and maintained in an upright position during the stability study. All of the containers were maintained at 5° C.±3° C., uninterrupted, (except for the addition or withdrawal of test samples) for a period of one, three, six, nine, or twelve months. Samples were removed at the specified time points and tested for carvedilol content. Testing of the stability samples was completed using High Performance Liquid Chromatography.

Shelf life of the oral liquid composition contained in the container closure system was estimated to be at least twelve months at the refrigerated testing conditions, based on the twelve month term stability assay results shown in Table 3. The stability assay of the oral liquid composition RD0013-067 in the 120 mL container closure system showed that 100 percent of the carvedilol was retained in the oral liquid composition stored under the refrigerated testing conditions for twelve months. As indicated in Table 3, an intermediate stability study of the oral liquid composition RD0013-067 was conducted over certain periods (one, three, six, nine, or twelve months) to determine the rate of physical or chemical degradation of the carvedilol in the oral liquid composition in the container closure system stored under intermediate testing conditions.

All stability samples (each sample comprising a container closure system including 120 mL of the oral liquid composition originally including 1.25 mg/mL of carvedilol) subjected to the intermediate testing conditions were placed upright in an environmental chamber and maintained in an upright position during the stability study. All of the containers were maintained at 30° C.±2° C. and 65%±5% RH, uninterrupted, (except for the addition or withdrawal of test samples) for a period of one, three, six, nine, or twelve months. Samples were removed from at the specified time points and tested for carvedilol content. Testing of the stability samples was completed using High Performance Liquid Chromatography.

Based on the twelve months term stability assay results shown in Table 3, shelf life of the oral liquid composition, RD0013-067, was estimated to be at least twelve months when stored at the intermediate testing conditions. The stability assay showed that 100% of the original carvedilol content was retained in the oral liquid composition stored under the intermediate testing conditions for twelve months.

As indicated in Table 3, an accelerated stability study of the oral liquid composition RD0013-067 in the container closure system stored under the accelerated testing conditions was conducted over certain periods (one, two, three, or six months) to determine the rate of physical or chemical degradation of the carvedilol in the oral liquid composition.

All stability samples (each sample comprising a container closure system including 120 mL of the oral liquid composition originally including 1.25 mg/mL of carvedilol) subjected to the accelerated testing conditions were placed upright in an environmental chamber and maintained in an upright position during the stability study. All of the containers were maintained at 40° C.±2° C. and 25%±5% RH, uninterrupted, (except for the addition or withdrawal of test samples) for a period of one, two, three, or nine months. Samples were removed at the specified time points and tested for carvedilol content. Testing of the stability samples was completed using High Performance Liquid Chromatography.

Based on the stability assay results shown in Table 3, shelf life of the oral liquid composition, RD0013-067, was estimated to be at least six months when stored at the accelerated testing conditions. The stability assay showed that 100 percent of the carvedilol was retained in the oral liquid composition stored under the accelerated testing conditions for six months.

Based on the results shown in Table 3, the inventor surprisingly discovered that the oral liquid composition including carvedilol, RD0013-067, in the container closure system retained 100% of the original content of carvedilol when stored under standard testing conditions of 25° C.±2° C. and 40%±5% relative humidity for eighteen months, under refrigerated testing conditions at 5° C.±3° C. for twelve months, and under intermediate testing conditions (30° C.±2° C. and 65%±5% relative humidity) for twelve months. Even under accelerated testing conditions (40° C.±2° C. and NMT 25% relative humidity) over the course of six months, the results showed retention of 100% of the original carvedilol content in the oral liquid composition.

Example 3. Preparation of Oral Liquid Compositions Including Carvedilol

Five different oral liquid compositions (composition Nos. 1-5) were prepared using the method for preparation of oral liquid composition RD0013-067. Table 4 shows the composition of the oral liquid composition No. 1, including 10.0 mg/mL of carvedilol, 10 mg/mL of hydroxypropyl beta-cyclodextrin, and 30.0 mg/mL of glacial acetic acid, with a balance of purified water.

Table 4. Composition of oral liquid composition No. 1 including 10.0 mg/mL carvedilol (1.0% w/w), 10 mg/mL hydroxypropyl beta-cyclodextrin (1.0% w/w), 30 mg/mL glacial acetic acid (3.0% w/w), and water (balance) at a pH of 3.5 (adjusted with glacial acetic acid).

TABLE 4

Composition of oral liquid composition No. 1 including 10.0 mg/mL carvedilol (1.0% w/w), 10 mg/mL hydroxypropyl beta-cyclodextrin (1.0% w/w), 30 mg/mL glacial acetic acid (3.0% w/w), and water (balance) at a pH of 3.5 (adjusted with glacial acetic acid).

| Ingredient | % w/w | mg/mL | pH |
|---|---|---|---|
| Carvedilol | 1.0 | 10 | 3.5 |
| Hydroxypropyl β-cyclodextrin | 1.0 | 10 | 3.5 |
| Glacial acetic acid | 3.0 | 30 | 3.5 |
| Purified water | balance | balance | 3.5 |
| Total | 100 | 1000 | 3.5 |

Table 5 shows the composition of oral liquid composition No. 2, including 2.5 mg/mL of carvedilol, 10 mg/mL of hydroxypropyl beta-cyclodextrin, and 0.2 mg/mL of glacial acetic acid, with a balance of purified water.

Table 5. Composition of oral liquid composition No. 2 including 2.5 mg/mL carvedilol (0.25% w/w), 10 mg/mL of hydroxypropyl beta-cyclodextrin (1.0% w/w), 0.2 mg/mL glacial acetic acid (0.02% w/w), and water (balance) at a pH of 3.5 (adjusted with glacial acetic acid).

TABLE 5

Composition of oral liquid composition No. 2 including 2.5 mg/mL carvedilol (0.25 % w/w), 10 mg/mL of hydroxypropyl beta-cyclodextrin (1.0% w/w), 0.2 mg/mL glacial acetic acid (0.02% w/w), and water (balance) at a pH of 3.5 (adjusted with glacial acetic acid).

| Ingredient | % w/w | mg/mL | pH |
|---|---|---|---|
| Carvedilol | 0.25 | 2.5 | 3.5 |
| Hydroxypropyl β-cyclodextrin | 1.0 | 10 | 3.5 |
| Glacial acetic acid | 0.02 | 0.2 | 3.5 |
| Purified water | balance | balance | 3.5 |
| Total | 100 | 1000 | 3.5 |

Table 6 shows the composition of the oral liquid composition No. 3, including 2.5 mg/mL of carvedilol, 20 mg/mL of hydroxypropyl beta-cyclodextrin, and 9.0 mg/mL of glacial acetic acid, with a balance of purified water.

Table 6. Composition of oral liquid composition No. 3 including 2.5 mg/mL carvedilol (0.25% w/w), 20 mg/mL hydroxypropyl beta-cyclodextrin (2.0% w/w), 9.0 mg/mL glacial acetic acid (0.9% w/w), and water (balance) at a pH of 3.5 (adjusted with glacial acetic acid).

TABLE 6

Composition of oral liquid composition No. 3 including 2.5 mg/mL carvedilol (0.25% w/w), 20 mg/mL hydroxypropyl beta-cyclodextrin (2.0% w/w), 9.0 mg/mL glacial acetic acid (0.9% w/w), and water (balance) at a pH of 3.5 (adjusted with glacial acetic acid).

| Ingredient | % w/w | mg/mL | pH |
|---|---|---|---|
| Carvedilol | 0.25 | 2.5 | 3.5 |
| Hydroxypropyl β-cyclodextrin | 2.0 | 20 | 3.5 |
| Glacial acetic acid | 0.9 | 9.0 | 3.5 |
| Purified water | balance | balance | 3.5 |
| Total | 100 | 1000 | 3.5 |

Table 7 shows the composition of oral liquid composition No. 4, including 2.5 mg/mL of carvedilol, 20 mg/mL of hydroxypropyl beta-cyclodextrin, and hydrochloric acid (0.1 N) in an amount sufficient to adjust the pH to 2.0, with a balance of purified water.

Table 7. Composition of oral liquid composition No. 4 including 2.5 mg/mL carvedilol (0.25% w/w), 20 mg/mL hydroxypropyl beta-cyclodextrin (2.0% w/w), and water (balance) at a pH of 2.0 (adjusted with HCl (1 N)).

TABLE 7

Composition of oral liquid composition No 4 including 2.5 mg/mL carvedilol (0.25% w/w), 20 mg/mL hydroxypropyl beta-cyclodextrin (2.0% w/w), and water (balance) at a pH of 2.0 (adjusted with HCl (1 N)).

| Ingredient | % w/w | mg/mL | pH |
|---|---|---|---|
| Carvedilol | 0.25 | 2.5 | 2.0 |
| Hydroxypropyl β-cyclodextrin | 2.0 | 20 | 2.0 |
| HCl (0.1N) | Quantum satis to adjust to pH 2.0 | Quantum satis to adjust to pH 2.0 | 2.0 |
| Purified water | balance | balance | 2.0 |
| Total | 100 | 1000 | 2.0 |

Table 8 shows the composition of oral liquid composition No. 5, including 1.25 mg/mL of carvedilol, 10 mg/mL of hydroxypropyl beta-cyclodextrin, and hydrochloric acid (0.1 N) in an amount sufficient to adjust the pH to 2.0, with a balance of purified water.

Table 8. Composition of oral liquid composition No. 5 including 1.25 mg/mL carvedilol (0.13% w/w), 10 mg/mL hydroxypropyl beta-cyclodextrin (1.0% w/w), and water (balance) at a pH of 2.0 (adjusted with HCl (0.1N)).

TABLE 8

Composition of oral liquid composition No. 5 including 1.25 mg/mL carvedilol (0.13% w/w), 10 mg/mL hydroxypropyl beta-cyclodextrin (1.0% w/w), and water (balance) at a pH of 2.0 (adjusted with HCl (0.1N)).

| Ingredient | % w/w | mg/mL | pH |
|---|---|---|---|
| Carvedilol | 0.13 | 1.25 | 2.0 |
| Hydroxypropyl β-cyclodextrin | 1.0 | 10 | 2.0 |
| HCl (0.1N) | Quantum satis to adjust to pH 2.0 | Quantum satis to adjust to pH 2.0 | 2.0 |
| Purified water | balance | balance | 2.0 |
| Total | 100 | 1000 | 2.0 |

Example 4

A study was conducted to assess the stability of the oral liquid composition Nos. 1-5, prepared in Example 3 including carvedilol, hydroxypropyl beta-cyclodextrin, glacial acetic acid or hydrochloric acid, and water. For purposes of conducting a stability study, 120 mL of each of the oral liquid composition Nos. 1-5 was packaged in the container closure system described in Example 3.

Four studies were conducted to assess the stability of the oral liquid compositions of oral liquid compositions Nos. 1-5, stored in the container closure system. The stability studies involved the following testing periods and conditions:

Standard testing conditions (25° C.±2° C. and 40%±5% RH) for up to six months.

Refrigerated testing conditions (5° C.±3° C.) for up to six months.

Intermediate testing conditions (30° C.±2° C. and 65%±5% RH) for up to six months.

Accelerated testing conditions (40° C.±2° C. and 25%±5% RH) for up to six months.

A stability study of the oral liquid composition contained in the container closure system and stored under standard testing conditions was conducted over a period of six months to determine the rate of physical or chemical degradation of the carvedilol included in each of the oral liquid compositions, Nos. 1-5.

All standard testing conditions stability samples (each sample consisting of a container closure system containing 120 mL of one of the oral liquid compositions, Nos. 1-5, each mL including 1.25 mg/mL, 2.5 mg/mL, or 10 mg/mL of carvedilol) were placed upright in a stability chamber and maintained in an upright position during the stability study. All of the containers were maintained at 25° C.±2° C. and 40%±5% relative humidity conditions, uninterrupted, (except for the addition or withdrawal of test samples) for a period of three or six months. Samples were removed from conditions at the specified time points and tested for carvedilol content. Storage of the stability samples was completed using a calibrated stability chamber. Testing of the stability samples was completed using High Performance Liquid Chromatography.

Table 9 reports stability data for the oral liquid composition Nos. 1-5, including 1.25 mg/mL, 2.5 mg/mL, or 10 mg/mL of carvedilol, stored under standard, testing conditions. In Table 9, $T_0$ refers to time zero.

Table 9. Stability results for the oral liquid composition Nos. 1-5, including 1.25 mg/mL, 2.5 mg/mL, or 10 mg/mL of carvedilol, in 120 mL bottles stored under standard testing conditions (25° C.±2° C. and 40%±5% RH) over a period of 3 or 6 months.

| Composition | Carvedilol mg/mL | Cyclodextrin mg/mL | pH | Assay Carvedilol % $T_0$ | Assay Carvedilol % 3 months | Assay Carvedilol % 6 months |
|---|---|---|---|---|---|---|
| 1 | 10 mg/mL | 10 mg/mL | 3.5 | 93.8 | 98.7 | 99.3 |
| 2 | 2.5 mg/mL | 10 mg/mL | 3.5 | 94.1 | 100.0 | 101.3 |
| 3 | 2.5 mg/mL | 20 mg/mL | 3.5 | 96.5 | 100.5 | 101.9 |
| 4 | 2.5 mg/mL | 20 mg/mL | 2.0 | 95.9 | 99.9 | 100.3 |
| 5 | 1.25 mg/mL | 10 mg/mL | 2.0 | 97.0 | 102.7 | 100.3 |

Based on the sixth month term stability assay results shown in Table 9 for the oral liquid composition Nos. 1-5, the shelf life of the oral liquid composition contained in each of the container closure systems was estimated to be at least six months under the standard testing conditions. The stability assay showed that greater than 99% percent of the original carvedilol was retained in the oral liquid composition in each of the 120 mL bottles over the course of storage at the standard testing conditions for six months.

A stability study of the oral liquid composition Nos. 1-5 contained in the container closure system and stored under refrigerated testing conditions was conducted over a period of six months to determine the rate of physical or chemical degradation of the carvedilol included in each of the oral liquid compositions, Nos. 1-5. All refrigerated testing conditions stability samples (each sample consisting of a container closure system containing 120 mL of one of the oral liquid compositions, Nos. 1-5, each mL including 1.25 mg/mL, 2.5 mg/mL, or 10 mg/mL of carvedilol) were placed upright in a calibrated stability chamber and maintained in an upright position during the stability study. All of the containers were maintained at 5° C. 3° C., uninterrupted, (except for the addition or withdrawal of test samples) for a period of three or six months. Samples were removed from conditions at the specified time points and tested for carvedilol content using High Performance Liquid Chromatography.

Table 10 reports stability data for the oral liquid composition Nos. 1-5, including 1.25 mg/mL, 2.5 mg/mL, or 10 mg/mL of carvedilol, stored under refrigerated, testing conditions. In Table 10, $T_0$ refers to time zero.

Table 10. Stability results for the oral liquid composition Nos. 1-5, including 1.25 mg/mL, 2.5 mg/mL, or 10 mg/mL of carvedilol, in 120 mL bottles stored under refrigerated testing conditions (5° C.±3° C.) over a period of 3 or 6 months.

| Composition | Carvedilol mg/mL | Cyclodextrin mg/mL | pH | Assay Carvedilol % $T_0$ | Assay Carvedilol % 3 months | Assay Carvedilol % 6 months |
|---|---|---|---|---|---|---|
| 1 | 10 mg/mL | 10 mg/mL | 3.5 | 93.8 | 101.2 | 98.3 |
| 2 | 2.5 mg/mL | 10 mg/mL | 3.5 | 94.1 | 102.8 | 100.3 |
| 3 | 2.5 mg/mL | 20 mg/mL | 3.5 | 96.5 | 102.2 | 99.9 |
| 4 | 2.5 mg/mL | 20 mg/mL | 2.0 | 95.9 | 101.3 | 99.6 |
| 5 | 1.25 mg/mL | 10 mg/mL | 2.0 | 97.0 | 102.4 | 99.6 |

Based on the six month term stability assay results shown in Table 9 for the oral liquid composition Nos. 1-5, the shelf life of the oral liquid composition contained in each of the container closure systems was estimated to be at least six months under the refrigerated testing conditions. The stability assay showed that greater than 98% percent of the original carvedilol was retained in the oral liquid composition in each of the 120 mL bottles over the course of storage at the refrigerated testing conditions for six months.

A stability study of the oral liquid composition Nos. 1-5 contained in the container closure system and stored under intermediate testing conditions was conducted over a period of six months to determine the rate of physical or chemical degradation of the carvedilol included in each of the oral liquid composition Nos. 1-5. All intermediate testing conditions stability samples (each sample consisting of a container closure system containing 120 mL of one of the oral liquid compositions, Nos. 1-5, each mL including 1.25 mg/mL, 2.5 mg/mL, or 10 mg/mL of carvedilol) were placed upright in a calibrated stability chamber and maintained in an upright position during the stability study. All of the containers were maintained at 30° C.±2° C. and 65%±5% relative humidity, uninterrupted, (except for the addition or withdrawal of test samples) for a period of three or six months. Samples were removed from conditions at the specified time points and tested for carvedilol content using High Performance Liquid Chromatography.

Table 11 reports stability data for the oral liquid composition Nos. 1-5, including 1.25 mg/mL, 2.5 mg/mL, or 10 mg/mL of carvedilol, stored under intermediate testing conditions. In Table 11, $T_0$ refers to time zero.

Table 11. Stability results for the oral liquid composition Nos. 1-5, including 1.25 mg/mL, 2.5 mg/mL, or 10 mg/mL of carvedilol, in 120 mL bottles stored under intermediate testing conditions (30° C.±2° C. and 65%±5% RH) over a period of 3 or 6 months.

| Composition | Carvedilol mg/mL | Cyclodextrin mg/mL | pH | Assay Carvedilol % $T_0$ | Assay Carvedilol % 3 months | Assay Carvedilol % 6 months |
|---|---|---|---|---|---|---|
| 1 | 10 mg/mL | 10 mg/mL | 3.5 | 93.8 | 98.5 | 99.0 |
| 2 | 2.5 mg/mL | 10 mg/mL | 3.5 | 94.1 | 99.4 | 100.8 |
| 3 | 2.5 mg/mL | 20 mg/mL | 3.5 | 96.5 | 100.2 | 100.2 |
| 4 | 2.5 mg/mL | 20 mg/mL | 2.0 | 95.9 | 101.4 | 100.4 |
| 5 | 1.25 mg/mL | 10 mg/mL | 2.0 | 97.0 | 102.8 | 100.4 |

Based on the six month term stability assay results shown in Table 11 for the oral liquid composition Nos. 1-5, the shelf life of the oral liquid composition contained in each of the container closure systems was estimated to be at least six months under the intermediate testing conditions. The stability assay showed that greater than 98% percent of the original carvedilol was retained in the oral liquid composition in each of the 120 mL bottles over the course of storage at the intermediate testing conditions for six months.

A stability study of the oral liquid composition Nos. 1-5 contained in the container closure system and stored under accelerated testing conditions was conducted over a period of six months to determine the rate of physical or chemical degradation of the carvedilol included in each of the oral liquid compositions, Nos. 1-5. All accelerated testing conditions stability samples (each sample consisting of a container closure system containing 120 mL of one of the oral liquid compositions, Nos. 1-5, each mL including 1.25 mg/mL, 2.5 mg/mL, or 10 mg/mL of carvedilol) were placed upright in a calibrated stability chamber and maintained in an upright position during the stability study. All of the containers were maintained at 40° C.±2° C. and 25%±5% relative humidity, uninterrupted (except for the addition or withdrawal of test samples), for a period of three or six months. Samples were removed from conditions at the specified time points and tested for carvedilol content using High Performance Liquid Chromatography.

Table 12 reports stability data for the oral liquid composition Nos. 1-5, including 1.25 mg/mL, 2.5 mg/mL, or 10 mg/mL of carvedilol, stored under accelerated, testing conditions. In Table 12, $T_0$ refers to time zero.

Table 12. Stability results for the oral liquid composition Nos. 1-5, including 1.25 mg/mL, 2.5 mg/mL, or 10 mg/mL of carvedilol, in 120 mL bottles stored under accelerated testing conditions (40° C.±2° C. and 25%±5% RH) over a period of 3 or 6 months.

| Composition | Carvedilol mg/mL | Cyclodextrin mg/mL | pH | Assay Carvedilol % $T_0$ | Assay Carvedilol % 3 months | Assay Carvedilol % 6 months |
|---|---|---|---|---|---|---|
| 1 | 10 mg/mL | 10 mg/mL | 3.5 | 93.8 | 100.0 | 102.0 |
| 2 | 2.5 mg/mL | 10 mg/mL | 3.5 | 94.1 | 101.0 | 103.8 |
| 3 | 2.5 mg/mL | 20 mg/mL | 3.5 | 96.5 | 101.5 | 103.9 |
| 4 | 2.5 mg/mL | 20 mg/mL | 2.0 | 95.9 | 101.1 | 102.8 |
| 5 | 1.25 mg/mL | 10 mg/mL | 2.0 | 97.0 | 103.2 | 102.7 |

Based on the six month term stability assay results shown in Table 12 for the oral liquid composition Nos. 1-5, the shelf life of the oral liquid composition contained in each of the container closure systems was estimated to be at least six months under the accelerated testing conditions. The stability assay showed that greater than 99% percent of the original carvedilol was retained in the oral liquid composition in each of the 120 mL bottles over the course of storage at the accelerated testing conditions for six months.

Example 5. Preparation of Oral Liquid Compositions Including Carvedilol

Four oral liquid compositions (Composition Nos. 6-9) including 1.25 mg/mL (0.125% w/w) carvedilol were prepared using the methods described below for solubility and stability testing and analysis. Table 13 shows the composition of oral liquid composition Nos. 6-9. Composition No. 10 is RD-0013-067 from Example and is provided below for comparison of the ingredients. Each oral liquid composition listed in Table 13 included 1.25 mg/mL (0.125% w/w) of carvedilol along with varied excipients.

Table 13. Compositions of oral liquid composition Nos. 6-10 including 1.25 mg/mL carvedilol (0.125% w/w) and varied excipients.

| Ingredient | Composition 6 % w/w | Composition 6 mg/mL | Composition 7 % w/w | Composition 7 mg/mL | Composition 8 % w/w | Composition 8 mg/mL | Composition 9 % w/w | Composition 9 mg/mL | Composition 10 (RD-0013-067) % w/w | Composition 10 (RD-0013-067) mg/mL |
|---|---|---|---|---|---|---|---|---|---|---|
| Carvedilol | 0.125 | 1.25 | 0.125 | 1.25 | 0.125 | 1.25 | 0.125 | 1.25 | 0.125 | 1.25 |
| Hydroxy Propyl β-cyclodextrin | 0.0 | 0.0 | 0.0 | 0.0 | 0.0 | 0.0 | 0.0 | 0.0 | 1.00 | 10.0 |
| Glacial acetic Acid | 0.0 | 0.0 | 0.0 | 0.0 | 0.0 | 0.0 | 0.0 | 0.0 | 0.160 | 1.60 |
| Purified Water | 0.0 | 0.0 | 0.0 | 0.0 | 0.0 | 0.0 | 0.0 | 0.0 | 98.7 | 987 |
| Sucralose | 0.680 | 6.80 | 0.500 | 5.00 | 0.680 | 6.80 | 0.680 | 6.80 | 0.0 | 0.0 |
| Anhydrous Citric Acid | 0.500 | 5.00 | 0.250 | 2.50 | 0.500 | 5.00 | 0.500 | 5.00 | 0.0 | 0.0 |
| Grape Flavor | 0.100 | 1.0 | 0.0 | 0.0 | 0.100 | 1.0 | 0.100 | 1.0 | 0.0 | 0.0 |
| Sodium Benzoate | 0.05 | 0.500 | 0.0 | 0.0 | 0.0 | 0.0 | 0.0 | 0.0 | 0.0 | 0.0 |
| Glycerin | 59.5 | 595 | 58.4 | 584 | 59.5 | 595 | 59.5 | 595 | 0.0 | 0.0 |
| Propylene Glycol | 18.9 | 189 | 14.0 | 140 | 18.7 | 187 | 18.9 | 189 | 0.0 | 0.0 |
| Ethanol | 9.68 | 96.8 | 9.68 | 96.8 | 9.68 | 96.8 | 9.68 | 96.8 | 0.0 | 0.0 |
| PEG 400 | 10.5 | 105 | 10.5 | 105 | 10.5 | 105 | 10.5 | 105 | 0.0 | 0.0 |
| Polysorbate 80 | 0.0 | 0.0 | 0.500 | 5.00 | 0.0 | 0.0 | 0.0 | 0.0 | 0.0 | 0.0 |
| Methyl Paraben | 0.0 | 0.0 | 0.200 | 2.00 | 0.0 | 0.0 | 0.0 | 0.0 | 0.0 | 0.0 |
| Propyl Paraben | 0.0 | 0.0 | 0.020 | 0.020 | 0.0 | 0.0 | 0.0 | 0.0 | 0.0 | 0.0 |
| Peppermint Oil | 0.0 | 0.0 | 5.8 | 58 | 0.0 | 0.0 | 0.0 | 0.0 | 0.0 | 0.0 |
| pH | 4.9 | | 4.8 | | 5.2 | | 4.8 | | 3.9 | |
| TOTAL | 100 | 1.00 | 100 | 1.00 | 100 | 1.00 | 100 | 1.00 | 100 | 1.00 |

Table 13 shows the composition of oral liquid composition No. 6, including 1.25 mg/mL carvedilol, 6.8 mg/mL sucralose, 5.0 mg/mL anhydrous citric acid, 1.0 mg/mL grape flavor, 0.5 mg/mL sodium benzoate, 595 mg/mL glycerin, 189 mg/mL propylene glycol, 96.8 mg/mL ethanol, and 105 mg/mL polyethylene glycol 400 (PEG 400).

Unless otherwise noted, all components of oral liquid composition Nos. 6 to 9 were added in the quantities/concentrations provided in Table 13 and steps were performed at standard testing conditions of no more than (NMT) 30° C. and NMT 85% relative humidity. To prepare composition No. 6, carvedilol was mixed with ethanol until the carvedilol was dissolved. In sequential steps each of the following ingredients were added, in the following order, one at a time, to the carvedilol/ethanol mixture with stirring until dissolved, sodium benzoate, sucralose, citric acid, grape flavor, propylene glycol, glycerin, and polyethylene glycol (PEG) 400 to form the oral liquid composition No. 6 of Table 13.

To prepare composition No. 7 methyl paraben was mixed with propylene glycol until the methyl paraben was dissolved. Next, in sequential steps each of the following ingredients were added, in the following order, one at a time to the methyl paraben/propylene glycol mixture with stirring until dissolved to form mixture A: propyl paraben, PEG 400, and citric acid. In a separate mixture, polysorbate 80 was mixed with ethanol until the polysorbate 80 was dissolved. Subsequently, each of the following ingredients were added, in the following order, one at a time to the polysorbate 80/ethanol mixture with stirring until dissolved to form mixture B: Carvedilol, sucralose, and peppermint oil. Next, mixture A was added with stirring to mixture B. Finally, glycerin was added to the A/B mixture to form composition No. 7 of Table 13.

To prepare composition No. 8 methyl paraben was mixed with propylene glycol until the methyl paraben was dissolved. Next, in sequential steps each of the following ingredients were added, in the following order, one at a time to the methyl paraben/propylene glycol mixture with stirring until dissolved to form mixture A: PEG 400, and citric acid. In a separate mixture, polysorbate 80 was mixed with ethanol with stirring. Subsequently, each of the following ingredients were added, in the following order, one at a time to the polysorbate 80/ethanol mixture with stirring until dissolved to form mixture B: Carvedilol, sucralose, and grape flavor. Next, mixture A was added with stirring to mixture B. Finally, glycerin was added to the A/B mixture to form composition No. 8 of Table 13.

To prepare composition No. 9 methyl paraben was mixed with propylene glycol until the methyl paraben was dissolved to form a mixture A. In a separate mixture, polysorbate 80 was mixed with ethanol with stirring. Subsequently, each of the following ingredients were added, in the following order, one at a time to the polysorbate 80/ethanol mixture with stirring until dissolved to form mixture B: carvedilol, sucralose, citric acid, and grape flavor. Next, mixture A was added with stirring to mixture B. Then glycerin was added with stirring to the A/B mixture. Finally, PEG 400 was added with stirring to the glycerin/A/B mixture to form composition No. 9 of Table 13.

Oral liquid composition No. 10 (also known as RD0013-067 in Example 1) was prepared as described in Example 1.

Example 6

A study was conducted to assess the solubility and stability of oral liquid composition Nos. 6-10 listed in Table 13, each of which included 1.25 mg/mL (0.125% w/w) carvedilol.

For purposes of conducting the solubility study, each of composition Nos. 6-10 included certain excipients that were observed to increase the solubility and stability of the oral liquid compositions. For example, as shown in Table 13, each of oral liquid composition Nos. 6-10 included one or more co-solvents, emulsifiers, and/or solubilizers. Additionally, the pH of oral liquid composition Nos. 6-10 was adjusted to a range of 3.9 to 5.2 and the effect on solubility and stability was observed. The inventors observed that the excipients added to each of oral liquid composition Nos. 6-10, in the adjusted pH range of 3.9 to 5.2, surprisingly increased solubility and yielded fully solubilized compositions. For example, the inventors observed that addition of glacial acetic acid to each of oral liquid composition Nos. 6-10 at pH values less than 5.2 resulted in a significant increase in the aqueous solubility of carvedilol.

For purposes of conducting the stability portion of the study, 120 mL of each of oral liquid composition Nos. 6-10 was packaged in the container closure system described in Example 3. Four studies were conducted to assess the stability of oral liquid composition Nos. 6-10 stored in the container closure system. The stability studies involved storing the compositions in the container closure system under the following conditions for the following time periods:

Standard testing conditions (25° C.±2° C. and 40%±5% RH) for up to eighteen months.

Refrigerated testing conditions (5° C.±3° C.) for up to twelve months.

Intermediate testing conditions (30° C.±2° C. and 65%±5% RH) for up to twelve months.

Accelerated testing conditions (40° C.±2° C. and 25%±5% RH) for up to six months.

A stability study of oral liquid compositions Nos. 6-10 contained in the container closure system and stored in a calibrated stability chamber under standard testing conditions was conducted over a period of six months to determine the rate of physical or chemical degradation of the carvedilol included in each of the oral liquid compositions.

All stability samples (each sample consisting of a container closure system containing 120 mL of one of the oral liquid composition Nos. 6-10) were placed upright in a stability chamber and maintained in an upright position during the stability study. All of the containers were maintained at 25° C.±2° C. and 40%±5% relative humidity, uninterrupted (except for the addition or withdrawal of test samples) for a period of one, three, six, nine, twelve, or eighteen months. Samples were removed from the containers at the specified time points and tested for carvedilol content using High Performance Liquid Chromatography.

Table 14 reports stability data for oral liquid composition Nos. 6-10 stored under standard testing conditions. To in Table 14 refers to time zero.

Table 14. Stability results for the oral liquid composition Nos. 6-10, including 1.25 mg/mL of carvedilol, in 120 mL bottles stored under standard testing conditions (25° C.±2° C. and 40%±5% RH) over a period of 1, 3, 6, 9, 12, or 18 months.

| Comp. No. | Carvedilol mg/mL | Assay | $T_0$ | 1 mo. | 3 mo. | 6 mo. | 9 mo. | 12 mo. | 18 mo. |
|---|---|---|---|---|---|---|---|---|---|
| 6 | 1.25 mg/mL | Carvedilol Percent | 98.9 | N/A | 95.4 | 89.0 | 95.1 | 93.1 | 95.5 |
|   |   | pH | 4.9 | N/A | 5.4 | 5.1 | 4.8 | 5.0 | 5.0 |
| 7 | 1.25 mg/mL | Carvedilol Percent | 79.0 | N/A | 95.5 | 92.9 | 89.7 | 86.4 | 90.0 |
|   |   | pH | 4.8 | N/A | 5.3 | 4.9 | 5.1 | 5.2 | 4.5 |
| 8 | 1.25 mg/mL | Carvedilol Percent | 99.2 | N/A | 97.4 | 93.0 | 94.0 | 91.5 | 95.6 |
|   |   | pH | 5.2 | N/A | 5.2 | 5.1 | 5.1 | 5.3 | 4.4 |
| 9 | 1.25 mg/mL | Carvedilol Percent | 99.7 | N/A | 94.9 | 93.1 | 102.6 | 95.4 | 96.0 |
|   |   | pH | 4.8 | N/A | 4.5 | 4.9 | 4.0 | 4.8 | 4.3 |
| 10 | 1.25 mg/mL | Carvedilol Percent | 106.5 | N/A | 103.0 | 103.4 | 102.6 | 105.3 | 106.1 |
|   |   | pH | 3.9 | N/A | 3.8 | 4.5 | 3.9 | 3.9 | 4.0 |

Based on the eighteen month term stability assay results shown in Table 14 for oral liquid composition No. 10, the shelf life of the oral liquid composition contained in the container closure systems was estimated to be at least eighteen months under the standard testing conditions. The stability assay showed that oral liquid composition No. 10 yielded the highest stability, with greater than 99% of the original amount of carvedilol retained in the oral liquid composition No. 10 samples in each of the 120 mL bottles over the eighteen months duration under standard testing conditions.

Oral liquid composition Nos. 6, 8, and 9 also exhibited substantial stability, retaining greater than 95% of the original amount of carvedilol in the stored samples over the eighteen month storage duration under standard testing conditions. Table 14 also shows that greater than 88% of the original amount of carvedilol was retained in the oral liquid composition No. 7 samples over the eighteen month storage duration under standard testing conditions. Thus, the eighteen month term stability assay results under standard testing conditions for oral liquid composition Nos. 6-9 ranged from 88.4% to 96.0% of the amount of carvedilol originally stored in the container closure system.

The inventors observed that oral liquid composition No. 10, which included 10 mg/mL hydroxy propyl beta cyclodextrin and 1.6 mg/mL glacial acetic acid (with a pH of 3.9), in addition to the 1.25 mg/mL of carvedilol, exhibited greater stability than oral liquid composition Nos. 6-9 when stored in the container closure system under standard testing conditions. The present inventors considered the improved stability of oral liquid composition No. 10 relative to composition Nos. 6-9 over the course of 12 and 18 months under the standard testing conditions surprising and unexpected given that composition No. 10 did not include a co-solvent as was present in composition Nos. 6-9. The present inventors attribute the enhanced solubility of carvedilol in composition No. 10 to the presence of cyclodextrin in the composition.

A stability study of oral liquid composition Nos. 6-10 contained in the container closure system and stored in a calibrated stability chamber under refrigerated testing conditions was conducted over a period of one, three, six, nine, or twelve months to determine the rate of physical or chemical degradation of the carvedilol in each of the oral liquid composition Nos. 6-10. All refrigerated testing condition stability samples (each sample including 120 mL of one of the oral liquid composition Nos. 6-10) were placed upright in a stability chamber and maintained in the upright position during the stability study. All of the containers were maintained at 5° C.±3° C., uninterrupted (except for the addition or withdrawal of test samples) for a period of one, three, six, nine, or twelve months. Samples were removed at the specified time points and tested for carvedilol content using High Performance Liquid Chromatography.

Table 15 reports stability data for the oral liquid composition Nos. 6-10 stored under refrigerated testing conditions. $T_0$ in Table 15 refers to time zero.

Table 15. Stability results for the oral liquid composition Nos. 6-10, including 1.25 mg/mL of carvedilol, in 120 mL bottles stored under refrigerated testing conditions (5° C.±3° C.) over a period of one, three, six, nine, or twelve months.

Based on the twelve month term stability study results shown in Table 15, the shelf life of the oral liquid compositions contained in each of the container closure systems was estimated to be at least twelve months under the refrigerated testing conditions. The stability assay showed that greater than 99% of the original carvedilol was retained in the oral liquid composition No. 10 (identical to composition RD-0013-067, of Example 1) over the course of storage at refrigerated testing conditions for twelve months.

The inventors unexpectedly observed that the oral liquid composition No. 10 yielded greater stability than oral liquid composition Nos. 6-9 when tested in the container closure system under refrigerated testing conditions for storage periods up to one month, up to three months, up to six months, up to nine months, or up to twelve months. Oral liquid composition Nos. 6, 7, and 8, tested over the course of three months showed that 97.2%, 97.4%, and 98.5%, respectively, of the original carvedilol content was retained in the oral liquid compositions over the course of storage at refrigerated testing conditions for three months. Oral liquid composition No. 10, which included 10 mg/mL hydroxy propyl beta cyclodextrin and 1.6 mg/mL glacial acetic acid (with a pH of 3.9) in addition to the 1.25 mg/mL of carvedilol in aqueous solution, yielded improved stability in comparison with oral liquid compositions 6-8. For example, the oral liquid composition No. 10 samples retained greater than 99% of the original carvedilol in each of the 120 mL bottles over the course of storage at refrigerated testing conditions for twelve months.

A stability study of the oral liquid composition Nos. 6-10 contained in the container closure system and stored under intermediate testing conditions was conducted over a period of twelve months to determine the rate of physical or chemical degradation of the carvedilol included in each of the oral liquid compositions. All intermediate testing conditions stability samples (each sample including a container closure system containing 120 mL of one of the oral liquid

| Comp. No. | Carvedilol mg/mL | Assay | $T_0$ | 1 mo. | 3 mo. | 6 mo. | 9 mo. | 12 mo. |
|---|---|---|---|---|---|---|---|---|
| 6 | 1.25 mg/mL | Carvedilol Percent | 98.9 | 93.6 | 97.2 | 98.4 | N/A | N/A |
|   |   | pH | 4.9 | 4.8 | 5.2 | 5.1 | N/A | N/A |
| 7 | 1.25 mg/mL | Carvedilol Percent | 79.0 | 92.0 | 97.4 | 96.4 | N/A | N/A |
|   |   | pH | 4.8 | 4.9 | 5.2 | 5.0 | N/A | N/A |
| 8 | 1.25 mg/mL | Carvedilol Percent | 99.7 | 95.4 | 98.5 | 99.2 | N/A | N/A |
|   |   | pH | 5.2 | 5.1 | 5.2 | 5.0 | N/A | N/A |
| 9 | 1.25 mg/mL | Carvedilol Percent | 99.7 | 95.3 | 96.9 | 93.7 | 100.7 | 96.7 |
|   |   | pH | 4.8 | 4.6 | 4.5 | 4.9 | 4.5 | 4.5 |
| 10 | 1.25 mg/mL | Carvedilol Percent | 106.5 | 99.2 | 100.4 | 96.0 | 103.7 | 105.2 |
|   |   | pH | 3.9 | 3.9 | 3.8 | 4.1 | 3.9 | 3.9 |

Based on the three-month term stability assay results shown in Table 15 for the oral liquid composition Nos. 6-8, the shelf life of the oral liquid composition contained in each of the container closure systems was estimated to be at least three months under the refrigerated testing conditions. The stability assay showed that greater than 97% percent of the original carvedilol was retained in the oral liquid composition in each of the 120 mL bottles over the course of storage at the refrigerated testing conditions for three months.

composition Nos. 6-10) were placed upright in a calibrated stability chamber and maintained in an upright position during the stability study. All of the containers were maintained at 30° C.±2° C. and 65%±5% relative humidity, uninterrupted, (except for the addition or withdrawal of test samples) for a period of one, three, six, nine, or twelve months. Samples were removed from conditions at the specified time points and tested for carvedilol content using High Performance Liquid Chromatography.

Table 16 reports stability data for the oral liquid composition Nos. 6-10, including 1.25 mg/mL of carvedilol, stored under intermediate testing conditions. $T_0$ refers to time zero in Table 16.

Table 16. Stability results for the oral liquid composition Nos. 6-10, including 1.25 mg/mL of carvedilol, in 120 mL bottles stored under intermediate testing conditions (30° C.±2° C. and 65%±5% RH) over a period of 1, 3, 6, 9, or 12 months.

| Comp. No. | Carvedilol mg/mL | Assay | $T_0$ | 1 mo. | 3 mo. | 6 mo. | 9 mo. | 12 mo. |
|---|---|---|---|---|---|---|---|---|
| 6 | 1.25 mg/mL | Carvedilol Percent | 98.9 | N/A | N/A | 94.7 | 94.7 | 77 |
|   |   | pH | 4.9 | N/A | N/A | 4.7 | 4.8 | 5.0 |
| 7 | 1.25 mg/mL | Carvedilol Percent | 79.0 | N/A | N/A | 93.9 | 91.6 | 87.8 |
|   |   | pH | 4.8 | N/A | N/A | 5.2 | 5.1 | 5.2 |
| 8 | 1.25 mg/mL | Carvedilol Percent | 99.7 | N/A | N/A | 93.2 | 95.1 | 93.1 |
|   |   | pH | 5.2 | N/A | N/A | 5.6// | 5.1 | 5.2 |
| 9 | 1.25 mg/mL | Carvedilol Percent | 99.7 | 93.7 | 93.7 | 93.8 | N/A | N/A |
|   |   | pH | 4.8 | 4.9 | 4.6 | 4.9 | N/A | N/A |
| 10 | 1.25 mg/mL | Carvedilol Percent | 106.6 | 100.4 | 103.1 | 102.5 | 95.4 | 104.7 |
|   |   | pH | 3.9 | 3.9 | 3.9 | 4.2 | 4.0 | 3.8 |

Based on the twelve-month term stability assay results shown in Table 16 for the oral liquid composition Nos. 6-10, the shelf life of the oral liquid composition in each of the container closure systems was estimated to be at least twelve months under the intermediate testing conditions. The stability assay showed that greater than 99% percent of the original carvedilol was retained in the oral liquid composition No. 10 in each of the 120 mL bottles over the course of storage at the intermediate testing conditions for twelve months.

The inventors unexpectedly observed that oral liquid composition No. 10 (identical to RD-0013-067 of Example 1), including 10 mg/mL hydroxy propyl beta cyclodextrin and 1.6 mg/mL glacial acetic acid (with a pH of 3.9) in addition to the 1.25 mg/mL of carvedilol, was fully solubilized (allowing for increased bioavailability of the active ingredient, carvedilol) and demonstrated substantially greater stability as compared to oral liquid composition Nos. 6, 7, and 8, when tested under intermediate conditions for twelve months. For example, Table 16 shows that oral liquid composition Nos. 6-8 tested over the course of twelve months resulted in retention of greater than 77% of the original carvedilol in the oral liquid compositions in each of the 120 mL bottles at intermediate testing conditions. In contrast, the stability assay results in Table 16 show that greater than 99% of the original amount of carvedilol was retained in the oral liquid composition No. 10 in each of the 120 mL bottles over the course of storage at the intermediate testing conditions for twelve months.

A stability study of the oral liquid composition Nos. 6-10 contained in the container closure system and stored under accelerated testing conditions was conducted over a period of six months to determine the rate of physical or chemical degradation of the carvedilol included in each of the oral liquid compositions. All accelerated testing conditions stability samples (each sample consisting of a container closure system containing 120 mL of one of the oral liquid compositions Nos. 6-10, each mL including 1.25 mg/mL of carvedilol) were placed upright in a calibrated stability chamber and maintained in an upright position during the stability study. All of the containers were maintained at 40° C.±2° C. and 25%±5% relative humidity, uninterrupted (except for the addition or withdrawal of test samples), for a period of one, two, three or six months. Samples were removed from conditions at the specified time points and tested for carvedilol content using High Performance Liquid Chromatography.

Table 17 reports stability data for the oral liquid composition Nos. 6-10, including 1.25 mg/mL of carvedilol, stored under accelerated, testing conditions. $T_0$ refers to time zero in Table 17.

Table 17. Stability results for the oral liquid composition Nos. 6-10, including 1.25 mg/mL of carvedilol, in 120 mL bottles stored under accelerated testing conditions (40° C.±2° C. and 25%±5% RH) over a period of one, two, three, or six months.

| Comp. No. | Carvedilol mg/mL | Assay | $T_0$ | 1 mo. | 2 mo. | 3 mo. | 6 mo. |
|---|---|---|---|---|---|---|---|
| 6 | 1.25 mg/mL | Carvedilol Percent | 98.9 | 95.5 | 92.0 | 93.9 | 87.3 |
|   |   | pH | 4.9 | 4.9 | 5.1 | 4.9 | 4.7 |
| 7 | 1.25 mg/mL | Carvedilol Percent | 79.0 | 92.5 | 89.8 | 95.2 | 93.7 |
|   |   | pH | 4.8 | 5.1 | 5.3 | 5.4 | 4.7 |
| 8 | 1.25 mg/mL | Carvedilol Percent | 99.7 | 95.4 | 92.8 | 94.5 | 90.0 |
|   |   | pH | 5.2 | 5.2 | 5.3 | 5.2 | 5.6 |
| 9 | 1.25 mg/mL | Carvedilol Percent | 99.7 | 92.2 | 95.0 | 97.3 | 94.2 |
|   |   | pH | 4.8 | 4.8 | 5.2 | 4.7 | 5.2 |
| 10 | 1.25 mg/mL | Carvedilol Percent | 106 | 101.6 | 103.4 | 92.7 | 103 |
|   |   | pH | 3.9 | 3.9 | 4.7 | 3.8 | 4.0 |

Based on the six month term stability assay results shown in Table 17 for the oral liquid composition Nos. 6-10, the shelf life of the oral liquid composition contained in each of the container closure systems was estimated to be at least six months under the accelerated testing conditions. The stability assay showed that greater than 99% of the original carvedilol was retained in the oral liquid composition No. 10 (identical to that of RD0013-067 of Example 1) in each of the 120 mL bottles over the course of storage at the accelerated testing conditions for six months.

The inventors surprisingly discovered that oral liquid composition No. 10 (identical to RD-0013-067 of Example 1), including 10 mg/mL hydroxy propyl beta cyclodextrin and 1.6 mg/mL glacial acetic acid (with a pH of 3.9) in addition to 1.25 mg/mL of carvedilol, demonstrated substantially greater stability as compared to oral liquid composition Nos. 6, 7, 8, and 9, when tested under accelerated conditions. For example, Table 17 shows that oral liquid composition Nos. 6-9 retained greater than 87% of the original carvedilol in the oral liquid compositions in each of the 120 mL bottles over the course of storage at accelerated testing conditions for six months. In contrast, the stability assay results shown in Table 17 show that greater than 99% of the original amount of carvedilol was retained in the oral liquid composition No. 10 in each of the 120 mL bottles over the course of storage at the accelerated testing conditions for six months.

Example 7. Preparation of Oral Liquid Composition Including Carvedilol

Based on the stability results discussed in Example 6, an additional oral liquid composition No. 11 including 2.50 mg/mL (0.25% w/w) carvedilol was prepared using the methods described below for solubility and stability testing and analysis. Table 18 shows the composition of oral liquid composition Nos. 10 and 11. Composition No. 10 is RD-0013-067 from Example 1 and is provided below for comparison of the ingredients.

Table 18. Composition of oral liquid composition Nos. 10 and 11 including 1.25 mg/mL carvedilol (0.125% w/w) or 2.50 mg/mL carvedilol (0.25% w/w) and varied excipients.

TABLE 18

Composition of oral liquid composition Nos. 10 and 11 including 1.25 mg/mL carvedilol (0.125% w/w) or 2.50 mg/mL carvedilol (0.25% w/w) and varied excipients.

|  | Composition 11 | | Composition 10 (RD-0013-067) | |
|---|---|---|---|---|
| Ingredient | % w/w | mg/mL | % w/w | mg/mL |
| Carvedilol | 0.25 | 2.50 | 0.125 | 1.25 |
| Hydroxy Propyl β-cyclodextrin | 2.00 | 20.0 | 1.00 | 10.0 |
| Sucralose | 0.680 | 6.80 | 0.0 | 0.0 |
| Hydrochloric acid (1N) | Adjust pH | Adjust pH | 0.0 | 0.0 |
| pH | 2-3 | 2-3 | 3.9 | 3.9 |
| Glacial acetic acid | 0.0 | 0.0 | 0.16 | 1.60 |
| Grape Flavor | 0.300 | 3.00 | 0.0 | 0.0 |
| Sorbitol Solution (70%) | 5.00 | 50.0 | 0.0 | 0.0 |
| Methyl paraben sodium | 0.17 | 1.70 | 0.0 | 0.0 |
| Propyl paraben sodium | 0.03 | 0.30 | 0.0 | 0.0 |
| Purified water | balance | balance | 98.7 | 987 |
| TOTAL | 100 | 1000 | 100 | 1000 |

Unless otherwise noted, all components of oral liquid composition No. 11 were added in the quantities/concentrations provided in Table 18 and steps were performed at standard testing conditions of no more than (NMT) 30° C. and NMT 85% relative humidity. To prepare composition No. 11 methyl paraben sodium was mixed with purified water with stirring until the methyl paraben sodium was dissolved. In sequential steps each of the following ingredients were added, in the following order, one at a time, to the methyl paraben sodium/water mixture with stirring, propyl paraben, sucralose, grape flavor, sorbitol solution and HCl to pH of 2-3 to form the oral liquid composition No. 11 of Table 18.

It will be understood that the present description illustrates those aspects of the invention relevant to a clear understanding of the invention. Certain aspects that would be apparent to those of ordinary skill in the art and that, therefore, would not facilitate a better understanding of the invention have not been presented in order to simplify the present description. Although only a limited number of embodiments of the present invention are necessarily described herein, one of ordinary skill in the art will, upon considering the foregoing description, recognize that many modifications and variations of the invention may be employed. All such variations and modifications of the invention are intended to be covered by the foregoing description and the following claims.

The following numbered clauses are directed to various non-limiting examples of inventions according to the present disclosure:

1. An oral liquid composition comprising:
   about 0.05 mg/mL to about 15.0 mg/mL carvedilol or a pharmaceutically acceptable salt or solvate thereof;
   about 1.0 mg/mL to about 50 mg/mL cyclodextrin;
   about 0.5 mg/mL to about 20 mg/mL acid; and
   water.
2. The oral liquid composition of clause 1, wherein the cyclodextrin comprises at least one of hydroxypropyl beta-cyclodextrin, sulfobutylether-beta-cyclodextrin, methyl-beta-cyclodextrin, polymeric derivatives of beta cyclodextrins, polyethylene glycol, and dextran-βCD.
3. The oral liquid composition of clause 1, wherein the cyclodextrin comprises hydroxypropyl beta-cyclodextrin.
4. The oral liquid composition of any of clauses 1 to 3, wherein the cyclodextrin ranges from about 7 mg/mL to about 30 mg/mL.
5. The oral liquid composition of any of clauses 1 to 4, wherein the acid comprises glacial acetic acid.
6. The oral liquid composition of any of clauses 1 to 4, wherein the acid comprises hydrochloric acid.
7. The oral liquid composition of any of clauses 1 to 6, wherein the carvedilol or a pharmaceutically acceptable salt or solvate thereof ranges from about 0.10 mg/mL to about 13.0 mg/mL.
8. The oral liquid composition of any of clauses 1 to 6, wherein the carvedilol or a pharmaceutically acceptable salt or solvate thereof ranges from about 0.07 mg/mL to about 3.0 mg/mL.
9. The oral liquid composition of any of clauses 1 to 8, wherein the carvedilol or a pharmaceutically acceptable salt or solvate thereof is fully solubilized in the oral liquid composition.
10. The oral liquid composition of any of clauses 1 to 8, wherein the carvedilol or a pharmaceutically acceptable salt or solvate thereof and the cyclodextrin are fully solubilized in the oral liquid composition.
11. The oral liquid composition of any of clauses 1 to 10, wherein the oral liquid composition is substantially free of solids.
12. The oral liquid composition of any of clauses 1 to 10, wherein the carvedilol or a pharmaceutically acceptable salt or solvate thereof is devoid of solid undissolved particulates.

13. The oral liquid composition of any of clauses 1 to 12, wherein the pH of the oral liquid composition is in a range of about 1.0 to about 5.0.
14. The oral liquid composition of any of clauses 1 to 12, wherein the pH of the oral liquid composition is in a range of about 2.0 to about 4.0.
15. The oral liquid composition of any of clauses 1 to 14, further comprising at least one of a sweetener, a flavoring agent, a stabilizer, a coloring agent, a thickener, and mixtures thereof.
16. The oral liquid composition of any of clauses 1 to 15, wherein the oral liquid composition retains at least about 90% of an initial carvedilol amount when stored at a temperature ranging from about 22° C. to about 28° C. and a relative humidity ranging from about 34% to about 47% for at least 18 months.
17. The oral liquid composition of any of clauses 1 to 15, wherein the oral liquid composition retains at least about 90% of an initial carvedilol amount when stored at a temperature ranging from about 22° C. to about 28° C. and a relative humidity ranging from about 34% to about 47% for at least 3 months.
18. The oral liquid composition of any of clauses 1 to 15, wherein the oral liquid composition retains at least about 90% of an initial carvedilol amount when stored at a temperature ranging from about 26° C. to about 34° C. and a relative humidity ranging from about 60% to about 70% for at least 3 months.
19. A method of treating hypertension comprising administering to a patient in need thereof an oral liquid composition comprising:
about 0.05 mg/mL to about 15.0 mg/mL carvedilol or a pharmaceutically acceptable salt or solvate thereof;
about 1.0 mg/mL to about 50 mg/mL cyclodextrin;
about 0.5 mg/mL to about 20 mg/mL acid; and
water.
20. The method of clause 19, wherein the carvedilol or a pharmaceutically acceptable salt or solvate thereof is fully solubilized in the oral liquid composition.
21. The method of clause 19, wherein the carvedilol or a pharmaceutically acceptable salt or solvate thereof and the cyclodextrin are fully solubilized in the oral liquid composition.
22. The method of any of clauses 19 to 21, wherein the cyclodextrin ranges from about 7 mg/mL to about 30 mg/mL.
23. The method of any of clauses 19 to 22, wherein the cyclodextrin comprises hydroxypropyl beta-cyclodextrin.
24. The method of any of clauses 19 to 23, wherein the acid comprises glacial acetic acid.
25. The method of any of clauses 19 to 24, wherein the oral liquid composition is substantially free of solids.
26. The method of any of clauses 19 to 25, wherein the pH of the oral liquid composition is in a range of about 1.0 to about 5.0.
27. The method of any of clauses 19 to 26, wherein the oral liquid composition retains at least about 90% of an initial carvedilol amount when stored at a temperature ranging from about 22° C. to about 28° C. and a relative humidity ranging from about 34% to about 47% for at least 18 months.
28. A method of treating heart failure comprising administering to a patient in need thereof an oral liquid composition comprising:
about 0.05 mg/mL to about 15.0 mg/mL carvedilol or a pharmaceutically acceptable salt or solvate thereof;
about 1.0 mg/mL to about 50 mg/mL cyclodextrin;
about 0.5 mg/mL to about 20 mg/mL acid; and
water.
29. The method of clause 28, wherein the oral liquid composition is substantially free of solids.
30. The method of any of clauses 28 and 29, wherein the carvedilol or a pharmaceutically acceptable salt or solvate thereof is fully solubilized in the oral liquid composition.
31. The method of any of clauses 28 and 29, wherein the carvedilol or a pharmaceutically acceptable salt or solvate thereof and the cyclodextrin are fully solubilized in the oral liquid composition.
32. The method of any of clauses 28 to 31, wherein the cyclodextrin ranges from about 7 mg/mL to about 30 mg/mL.
33. The method of any of clauses 28 to 32, wherein the cyclodextrin comprises hydroxypropyl beta-cyclodextrin.
34. The method of any of clauses 28 to 33, wherein the acid comprises glacial acetic acid.
35. The method of any of clauses 28 to 34, wherein the pH of the oral liquid composition is in a range of about 1.0 to about 5.0.
36. The method of any of clauses 28 to 35, wherein the oral liquid composition retains at least about 90% of an initial carvedilol amount when stored at a temperature ranging from about 22° C. to about 28° C. and a relative humidity ranging from about 34% to about 47% for at least 3 months.
37. A method of reducing cardiovascular mortality in clinically stable patients with left ventricular failure or left ventricular dysfunction following myocardial infarction comprising administering to a patient in need thereof an oral liquid composition comprising:
about 0.05 mg/mL to about 15.0 mg/mL carvedilol or a pharmaceutically acceptable salt or solvate thereof;
about 1.0 mg/mL to about 50 mg/mL cyclodextrin;
about 0.5 mg/mL to about 20 mg/mL acid; and
water.
38. The method of clause 37, wherein the carvedilol or a pharmaceutically acceptable salt or solvate thereof is fully solubilized in the oral liquid composition.
39. The method of clause 37, wherein the carvedilol or a pharmaceutically acceptable salt or solvate thereof and the cyclodextrin are fully solubilized in the oral liquid composition.
40. The method of any of clauses 37 to 39, wherein the cyclodextrin ranges from about 7 mg/mL to about 30 mg/mL.
41. The method of any of clauses 37 to 40, wherein the cyclodextrin comprises hydroxypropyl beta-cyclodextrin.
42. The method of any of clauses 37 to 41, wherein the acid comprises glacial acetic acid.
43. The method of any of clauses 37 to 42, wherein the oral liquid composition is substantially free of solids.
44. The method of any of clauses 37 to 44, wherein the pH of the oral liquid composition is in a range of about 1.0 to about 5.0.
45. The method of any of clauses 37 to, wherein the oral liquid composition retains at least about 90% of an initial carvedilol amount when stored at a temperature ranging from about 22° C. to about 28° C. and a relative humidity ranging from about 34% to about 47% for at least 3 months.

What is claimed is:

1. An oral liquid composition comprising:
   about 0.05 mg/mL to about 15.0 mg/mL carvedilol or a pharmaceutically acceptable salt or solvate thereof;
   about 1.0 mg/mL to about 50 mg/mL cyclodextrin;
   about 0.0020 mg/mL to about 38 mg/mL acid; and
   water;
   wherein the oral liquid composition retains at least about 90% of an initial amount of carvedilol or pharmaceutically acceptable salt or solvate thereof when stored at a temperature ranging from about 38° C. to about 42° C. and a relative humidity not more than 25% for at least 3 months.

2. The oral liquid composition of claim 1, wherein the carvedilol or pharmaceutically acceptable salt or solvate thereof ranges from about 7.5 mg/mL to about 12.5 mg/mL.

3. The oral liquid composition of claim 1, wherein the carvedilol or pharmaceutically acceptable salt or solvate thereof ranges from about 0.80 mg/mL to about 3.0 mg/mL.

4. The oral liquid composition of claim 1, wherein the oral liquid composition retains at least about 90% of an initial amount of carvedilol or pharmaceutically acceptable salt or solvate thereof when stored at a temperature ranging from about 38° C. to about 42° C. and a relative humidity not more than 25% for at least 6 months.

5. The oral liquid composition of claim 1, wherein the cyclodextrin comprises at least one of hydroxypropyl beta-cyclodextrin, sulfobutylether-beta-cyclodextrin, methyl-beta-cyclodextrin, polymeric derivatives of beta cyclodextrins, βCD-PEG, and dextran-βCD.

6. The oral liquid composition of claim 1, wherein the cyclodextrin comprises hydroxypropyl beta-cyclodextrin.

7. The oral liquid composition of claim 1, wherein the cyclodextrin ranges from about 7.0 mg/mL to about 30 mg/mL.

8. The oral liquid composition of claim 1, wherein the acid comprises glacial acetic acid.

9. The oral liquid composition of claim 1, wherein the acid comprises hydrochloric acid.

10. The oral liquid composition of claim 2, wherein the carvedilol or pharmaceutically acceptable salt or solvate thereof is fully solubilized in the oral liquid composition.

11. The oral liquid composition of claim 3, wherein the carvedilol or pharmaceutically acceptable salt or solvate thereof is fully solubilized in the oral liquid composition.

12. The oral liquid composition of claim 4, wherein the carvedilol or pharmaceutically acceptable salt or solvate thereof is fully solubilized in the oral liquid composition.

13. The oral liquid composition of claim 1, wherein the carvedilol or pharmaceutically acceptable salt or solvate thereof and the cyclodextrin are fully solubilized in the oral liquid composition.

14. The oral liquid composition of claim 1, wherein the pH of the oral liquid composition is in a range of about 1.0 to about 5.0.

15. The oral liquid composition of claim 1, wherein the pH of the oral liquid composition is in a range of about 1.5 to about 4.0.

16. The oral liquid composition of claim 1, wherein the oral liquid composition retains at least about 92% of an initial amount of carvedilol or pharmaceutically acceptable salt or solvate thereof when stored at a temperature ranging from about 38° C. to about 42° C. and a relative humidity not more than 25% for at least 3 months.

17. The oral liquid composition of claim 1, wherein the oral liquid composition retains at least about 92% of an initial amount of carvedilol or pharmaceutically acceptable salt or solvate thereof when stored at a temperature ranging from about 38° C. to about 42° C. and a relative humidity not more than 25% for at least 6 months.

18. An oral liquid composition comprising:
    about 0.05 mg/mL to about 15.0 mg/mL carvedilol or a pharmaceutically acceptable salt or solvate thereof;
    about 1.0 mg/mL to about 50 mg/mL cyclodextrin, wherein the cyclodextrin comprises at least one of hydroxypropyl beta-cyclodextrin, sulfobutylether-beta-cyclodextrin, methyl-beta-cyclodextrin, polymeric derivatives of beta cyclodextrins, βCD-PEG, and dextran-βCD;
    about 0.0020 mg/mL to about 38 mg/mL acid, wherein the acid comprises at least one of glacial acetic acid and hydrochloric acid; and
    water;
    wherein the pH of the oral liquid composition is in a range of about 1.0 to about 5.0; and
    wherein the oral liquid composition retains at least about 90% of an initial amount of carvedilol or pharmaceutically acceptable salt or solvate thereof when stored at a temperature ranging from about 38° C. to about 42° C. and a relative humidity not more than 25% for at least 3 months.

19. The oral liquid composition of claim 18, wherein the carvedilol or pharmaceutically acceptable salt or solvate thereof is fully solubilized in the oral liquid composition.

20. The oral liquid composition of claim 18, wherein the oral liquid composition retains at least about 92% of an initial amount of carvedilol or pharmaceutically acceptable salt or solvate thereof when stored at a temperature ranging from about 38° C. to about 42° C. and a relative humidity not more than 25% for at least 3 months.

21. The oral liquid composition of claim 18, wherein the oral liquid composition retains at least about 90% of an initial amount of carvedilol or pharmaceutically acceptable salt or solvate thereof when stored at a temperature ranging from about 38° C. to about 42° C. and a relative humidity not more than 25% for at least 6 months.

22. A method of treating hypertension comprising administering to a patient in need thereof an oral liquid composition comprising:
    about 0.05 mg/mL to about 15.0 mg/mL carvedilol or a pharmaceutically acceptable salt or solvate thereof;
    about 1.0 mg/mL to about 50 mg/mL cyclodextrin;
    about 0.0020 mg/mL to about 38 mg/mL acid; and
    water;
    wherein the oral liquid composition retains at least about 90% of an initial amount of carvedilol or pharmaceutically acceptable salt or solvate thereof when stored at a temperature ranging from about 38° C. to about 42° C. and a relative humidity not more than 25% for at least 3 months.

23. The method of claim 22, wherein the carvedilol or pharmaceutically acceptable salt or solvate thereof ranges from about 0.80 mg/mL to about 3.0 mg/mL.

24. The method of claim 22, wherein the carvedilol or a pharmaceutically acceptable salt or solvate thereof is fully solubilized in the oral liquid composition.

25. The method of claim 22, wherein the oral liquid composition retains at least about 90% of an initial amount of carvedilol or pharmaceutically acceptable salt or solvate thereof when stored at a temperature ranging from about 38° C. to about 42° C. and a relative humidity not more than 25% for at least 6 months.

26. A method of treating heart failure comprising administering to a patient in need thereof an oral liquid composition comprising:
- about 0.05 mg/mL to about 15.0 mg/mL carvedilol or a pharmaceutically acceptable salt or solvate thereof;
- about 1.0 mg/mL to about 50 mg/mL cyclodextrin;
- about 0.0020 mg/mL to about 38 mg/mL acid; and
- water;
- wherein the oral liquid composition retains at least about 90% of an initial amount of carvedilol or pharmaceutically acceptable salt or solvate thereof when stored at a temperature ranging from about 38° C. to about 42° C. and a relative humidity not more than 25% for at least 3 months.

27. The method of claim 26, wherein the carvedilol or pharmaceutically acceptable salt or solvate thereof ranges from about 0.80 mg/mL to about 3.0 mg/mL.

28. The method of claim 26, wherein the carvedilol or a pharmaceutically acceptable salt or solvate thereof is fully solubilized in the oral liquid composition.

29. The method of claim 26, wherein the oral liquid composition retains at least about 90% of an initial amount of carvedilol or pharmaceutically acceptable salt or solvate thereof when stored at a temperature ranging from about 38° C. to about 42° C. and a relative humidity not more than 25% for at least 6 months.

30. The oral liquid composition of claim 1, wherein the carvedilol or pharmaceutically acceptable salt or solvate thereof is fully solubilized in the oral liquid composition.

* * * * *